US009493550B2

(12) United States Patent
Ikuta et al.

(10) Patent No.: US 9,493,550 B2
(45) Date of Patent: Nov. 15, 2016

(54) HUMAN ANTI-HUMAN INFLUENZA VIRUS ANTIBODY

(71) Applicants: Osaka University, Osaka (JP); The Research Foundation for Microbial Diseases of Osaka University, Osaka (JP)

(72) Inventors: Kazuyoshi Ikuta, Osaka (JP); Ritsuko Koketsu, Osaka (JP); Yoshinobu Okuno, Kagawa (JP); Mikihiro Yunoki, Osaka (JP); Shoji Ideno, Osaka (JP); Masatoshi Oshita, Osaka (JP); Motoki Kuhara, Nagano (JP); Masatoshi Momota, Nagano (JP)

(73) Assignees: Osaka University, Osaka (JP); The Research Foundation for Microbial Diseases of Osaka University, Osaka (JP)

( * ) Notice: Subject to any disclaimer, the term of this patent is extended or adjusted under 35 U.S.C. 154(b) by 104 days.

(21) Appl. No.: 14/505,515

(22) Filed: Oct. 3, 2014

(65) Prior Publication Data

US 2015/0044225 A1 Feb. 12, 2015

Related U.S. Application Data

(63) Continuation of application No. 13/141,998, filed as application No. PCT/JP2009/007159 on Dec. 24, 2009, now Pat. No. 8,975,378.

(30) Foreign Application Priority Data

Dec. 25, 2008 (JP) ................................ 2008-330425
Jun. 19, 2009 (JP) ................................ 2009-146832

(51) Int. Cl.
*C07K 16/10* (2006.01)
*A61K 39/00* (2006.01)

(52) U.S. Cl.
CPC ..... *C07K 16/1018* (2013.01); *A61K 2039/505* (2013.01); *C07K 2317/14* (2013.01); *C07K 2317/21* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| 5,684,146 A | 11/1997 | Okuno et al. |
| 6,720,409 B2 | 4/2004 | Okuno et al. |
| 2011/0319600 A1 | 12/2011 | Ikuta et al. |

FOREIGN PATENT DOCUMENTS

| JP | 07-304799 | 11/1995 |
| JP | 2006-254777 | 9/2006 |
| WO | 84/00687 A1 | 3/1984 |

OTHER PUBLICATIONS

Zahradnik et al. Serum neutralizing antibody and lymphocyte transformation responses after influenza B virus infections. J Clin Microbiol. Nov. 1983;18(5):1266-8.*
Wrammert et al. Rapid cloning of high-affinity human monoclonal antibodies against influenza virus. Nature, 2008, 453:667-672.*
Yu et al. An optimized electrofusion-based protocol for generating virus-specific human monoclonal antibodies. J Immunol Methods. Jul. 31, 2008;336(2):142-151. Epub May 5, 2008.*
Shibuya et al., "Identification of a human monoclonal Fab with neutralizing activity against H3N2 influenza A strain from a newly constructed human Fab library," Microbiol. Immunol., vol. 52, No. 3, 2008, pp. 162-170 (9 pages).
Atassi et al., "Localization, synthesis, and activity of an antigenic site on influenza virus hemagglutinin," Proc. Natl. Acad. Sci. USA, vol. 80, No. 3, 1983, pp. 840-844 (5 pages).
Kubota-Koketsu et al., "Broad neutralizing human monoclonal antibodies against influenza virus from vaccinated healthy donors," Biochemical and Biophysical Research Communications, vol. 387, No. 1, Sep. 11, 2009, pp. 180-185 (6 pages).
Green et al., "Immunogenic Structure of the Influenza Virus Hemagglutinin," Cell, vol. 28, Mar. 1982, pp. 477-487 (11 pages).
Wiley et al., "The Structure and Function of the Hemagglutinin Membrane Glycoprotein of Influenza Virus," Ann. Rev. Biochem, vol. 56, 1987, pp. 365-394 (30 pages).
International Search Report issued in corresponding International Patent Application No. PCT/JP2009/007159, dated Feb. 2, 2010 (2 pages).
Wrammert et al., "Rapid cloning of high-affinity human monoclonal antibodies against influenza virus," NIH Public Access Author Manuscript, (pp. 1-15); Published in final edited form as Nature, 453 (7195), May 29, 2008, pp. 667-671.
Wrammert et al., Supplementary data for: "Rapid Cloning of High Affinity Human Monoclonal Antibodies Against Influenza Virus," Internet download, publication date unknown, pp. 1-19.

(Continued)

*Primary Examiner* — Nick Zou
(74) *Attorney, Agent, or Firm* — Kilyk & Bowersox, P.L.L.C.

(57) ABSTRACT

Provided is a human antibody having a neutralization activity against a human influenza virus. More specifically, provided is a human antibody which recognizes a highly conserved region in a human influenza A virus subtype H3N2 or a human influenza B virus and has a neutralization activity against the virus. The human antibody is a human anti-human influenza virus antibody, which has a neutralization activity against a human influenza A virus subtype H3N2 and binds to a hemagglutinin HA1 region of the human influenza A virus subtype H3N2, or which has a neutralization activity against a human influenza B virus, and includes, as a base sequence of a DNA encoding a variable region of the antibody, a sequence set forth in any one of SEQ ID NOS: 5 to 12.

12 Claims, 18 Drawing Sheets

(56) References Cited

OTHER PUBLICATIONS

Japanese Office Action dated Jun. 4, 2014 from counterpart Japanese Patent Application No. 2010-543870 with English translation (11 pages).
Extended European Search Report dated Oct. 10, 2012 from counterpart European Patent Application No. 09834454.2 (11 pages).
Knossow et al., "Mechanism of neutralization of influenza virus infectively by antibodies," Virology, Oct. 2002; 302(2): 294-298.
Okuno et al., "Analysis for properties of human monoclonal antibodies using influenza vaccine strains, Research on preparation of human antibodies for emergency therapeutic medicine," General Overview and Report for Shared research in the 17 year of the Heisei era, 2006, pp. 8-15 (with English translation).
Office Action received in Control No. 96/000,118 (U.S. Pat. No. 8,975,378) dated Mar. 21, 2016 (16 pages).
GenBank AB847411 Influenza A virus (A/Aichi/2-1/1968(H3N2) HA gene for hemagglutinin precursor, complete cds (2 pages).
Iba et al., "Conserved Neutralizing Epitope at Globular Head of Hemagglutinin in H3N2 Influenza Viruses," Journal of Virology, vol. 88, No. 13, Jul. 2014, pp. 7130-7144.
Hashem, A.M., "Prospects of HA-Based Universal Influenza Vaccine," BioMed Research International, vol. 2015, Article ID 414637, pp. 1-12.
Sun et al., "Large-scale analysis of B-cell epitopes on influenza virus hemagglutinin—implications for cross-reactivity of neutralizing antibodies," Frontiers in Immunology, vol. 5, Article 38, Feb. 2014, pp. 1-12.
Smith et al., "Use of Human Hybridoma Technology to Isolate Human Monoclonal Antibodies," Microbiology Spectrum, Jan. 30, 2015, pp. 1-12.
Corrected Request for Supplemental Examination filed Oct. 27, 2015 (Control No. 96/000,118; U.S. Pat. No. 8,975,378) (70 pages).

\* cited by examiner

Figure 2
A) AH3N2
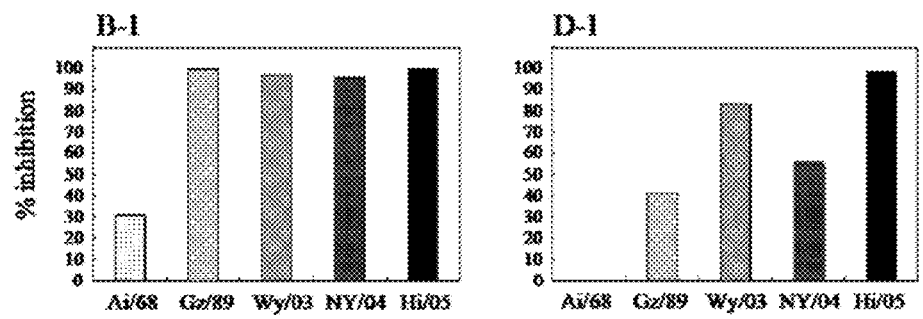
B) B
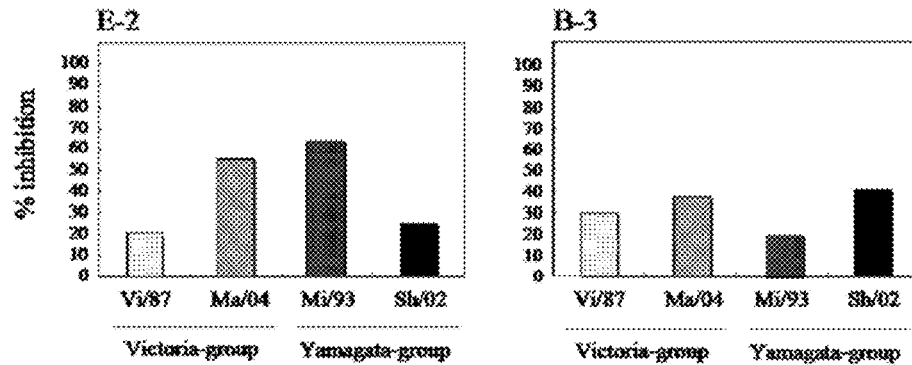

Figure 4

● B-1 (H3 RECOGNITION)
[L CHAIN] VARIABLE REGION BASE SEQUENCE (SEQ ID NO: 20)

\* AN UNDERLINED PORTION DENOTES THE VARIABLE REGION OF SEQ ID NO: 6 IN SEQUENCE LISTING.

```
         10        20        30        40        50        60        70        80        90       100       110       120
AAGCAGTGGTATCAACGCAGAGTACGCGGGGAGTTCAGTCAGGACACAGCGTGGACATGAGGGTCCCCGCTCAGCTCCTGGGGCTCCTGCTACTCTGGCTCCGAGTGCCAGTGGTGAC
                                                            M  R  V  P  A  Q  L  L  L  L  W  L  R  G  A  S  G  D
                                                            SIGNAL                                       N-TERMINAL
                                                                                                        (SEQ ID NO:28)
        130       140       150       160       170       180       190       200       210       220       230       240
GTCCAGATGACTCAGTCTCCATCTCCCTGTCTGCATCTGTGGGAGACAGAGTCACCATCACTTGTCGGGCAAGTCAGAGCGTTGAGCAATTATGGTAATTGGTATCAACAGAAGCCAGGG
 V  Q  M  T  Q  S  P  S  S  L  S  A  S  V  G  D  R  V  T  I  T  C  R  A  S  Q  S  V  S  N  Y  V  N  W  Y  Q  Q  K  P  G
                                                                     CDR1
                                                                  (SEQ ID NO:38)
        250       260       270       280       290       300       310       320       330       340       350       360
AGAGCCCCTAGGCTCCTCATCTATGCTGCGTCCAATCTAGTGGCGGGTCCCCGGTTCAGTGGCAGTGGGTCTGGGACAGACTTCACTCTCACCATCACCAGTCTGCAACCTGAA
 R  A  P  R  L  L  I  S  S  A  S  N  L  W  A  G  V  P  P  R  F  S  G  R  G  E  E  T  D  F  T  L  T  I  T  S  L  Q  P  E
                    CDR2
                 (SEQ ID NO:39)
        370       380       390       400       410       420       430       440       450       460       470       480
GATTCTGCAGTTTACTACTGTCAACAGAGTTACAGTGACCTTCTCAGTTTCGGCGGAGGGACCAAGGTGGAGATCAAACGAACTGTGGCTGCACCATCTGTCTTCATCTTCCCGCCATCT
 D  S  A  V  Y  Y  C  Q  Q  S  Y  S  D  L  L  S  F  G  G  G  T  K  V  E  I  K  R  T  V  A  A  P  S  V  F  I  F  P  P  S
                    CDR3                                                                              CL
                 (SEQ ID NO:40)
        490       500       510       520       530       540       550       560       570       580       590       600
GATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAG
 D  E  Q  L  K  S  G  T  A  S  V  V  C  L  L  N  N  F  Y  P  R  E  A  K  V  Q  W  K  V  D  N  A  L  Q  S  G  N  S  Q  E
                                                                                                   (SEQ ID NO:78)
        610       620
AGTGTCACAGAGCAGGACAGCAAGGACACAG
 S  V  T  E  Q  D  S  K  D
```

Figure 5

● D-1 (H3 RECOGNITION)
[H CHAIN] VARIABLE REGION BASE SEQUENCE (SEQ ID NO: 21)    * AN UNDERLINED PORTION DENOTES THE VARIABLE REGION OF SEQ ID NO: 7 IN SEQUENCE LISTING.

```
         10        20        30        40        50        60        70        80        90       100       110       120
CTAATACGACTCACTATAGGGCAAGCAGTGGTATCAACGCAGAGTACGCGGGGACCCAACAACCACACCCCTCCTAAGAAGAAGCCCCTAGACCACCAGCTCCACACCATGACTGGACCT
                                                                                                            M  D  W  T  W
        130       140       150       160       170       180       190       200       210       220       230       240
GGAGGATCCTCTCTTCTTGGTGGCAGCAGCAACAGGTGCCCACTCCCAGGTGCAGCTGGTGCAATCTGGGTCTGAGTTGAAGAAGCCTGGGGCCTCAGTGAAGGTTTCCTGCAAGGCTTCTG
 R  I  L  F  L  V  A  A  A  T  G  A  H  S  Q  V  Q  L  V  Q  S  G  S  E  L  K  K  P  G  A  S  V  K  V  S  C  K  A  S  G
                                                     N-TERMINAL ▲ (SEQ ID NO:29)
        250       260       270       280       290       300       310       320       330       340       350       360
GATACACCTTCACCTCTTATTCTATATATTGGGTGCGACAGGCCCCTGACACAGGGGCTTGAGTGGATGGATGGAATGGGATGGATCAACAACACTGGAAACCCAAGCTATGCCCAGGGCTTCACAG
 Y  T  F  T  S  Y  S  I  Y  W  V  R  Q  A  P  G  Q  G  L  E  W  M  G  W  I  N  T  N  T  G  N  P  S  Y  A  Q  G  F  T  G
       CDR1 ━━━▶                                                                           ◀━━━ CDR2 ━━━▶
       (SEQ ID NO:41)                                                                           (SEQ ID NO:42)
        370       380       390       400       410       420       430       440       450       460       470       480
GACGGGTTTGTCTTCTCCTTTGACACCTCTGTCAGCACGGCCATATCTGGAGATCAGCACGGCCTAAAGGCTGAGGACACTGCCGTGTATTACTGTGCGAGAGAGGGAGATTACGATATTTGA
 D  G  F  V  F  S  F  D  T  S  V  S  T  A  Y  L  E  I  S  S  L  K  A  E  D  T  A  V  Y  Y  C  A  R  E  G  D  Y  D  I  L
                                                                                                  ◀━━━ CDR3 ━━━━━
        490       500       510       520       530       540       550       560       570       580       590       600
CTGGTTATTATTACTTTGACTACTGGGGCCAAGGGAACCCTGGTCACCGTCTCCTCAGCCTCCACCAAGGGCCCATCGGTCTTCCCCCTGGCACCCTCCTCCAAGAGCACCTCTGGGG
 T  G  Y  Y  Y  Y  F  D  Y  W  G  Q  G  T  L  V  T  V  S  S  A  S  T  K  G  P  S  V  F  P  L  A  P  S  S  K  S  T  S  G  G
                                                       CH1
                                                                 (SEQ ID NO-43)
        610       620       630       640       650       660       670       680       690       700
GCACAGCGGCCCTGGGCTGCCTGGTCAAGGACTACTTCCCCGAACCGGTGACGGTGTCGTGGAACTCAGGCGCCCTGACCAGCGGCGTGCACACCTT
 T  A  A  L  G  C  L  V  K  D  Y  F  P  E  P  V  T  V  S  W  N  S  G  A  L  T  S  G  V  H  T  (SEQ ID NO:79)
```

● B-3 (B RECOGNITION)
[L CHAIN] VARIABLE REGION BASE SEQUENCE (SEQ ID NO: 26)

* AN UNDERLINED PORTION DENOTES THE VARIABLE REGION OF SEQ ID NO: 12 IN SEQUENCE LISTING.

```
       10        20        30        40        50        60        70        80        90       100       110       120
GTAATAGGACTGACTGTAGGGACTGCAAGCAGTGGTTCAACGCAGAGATAGGCGGGAAGCAAGTACGGCGGGGAGGTTGAGGTGTGGGGTAGAGAGACAGGACTGAGGAC
*  Y  D  S  L  *  G  K  Q  W  Y  Q  R  R  V  R  G  K  Q  W  Y  Q  R  R  V  R  G  E  L  Q  L  W  V  E  K  T  G  L  R  T
      130       140       150       160       170       180       190       200       210       220       230       240
AGTCTCGAAGCATGGCCAGCTTCCGTCTCCTCGTCACTCTGCTTCTCACTCATCGCAGGAAGTCCTCGAGGTCCTGCTCGCTTCCTCAGGCTCTGGGACCCCGGCGCAGAGGGT
L  S  S  M  A  S  F  P  L  L  L  T  L  L  T  H  C  A  G  S  W  A  Q  S  V  L  A  Q  P  P  S  A  S  G  T  P  G  Q  R  V
                leader                                              N-TERMINAL
                                                                   (SEQ ID NO:34)
      250       260       270       280       290       300       310       320       330       340       350       360
CATCATCTCCTTGTGTGGAACGTTGGTCCAAGATCGGGAGTAATTGTGTCAACTGGTACCAGGAGACGCCCGAGGGCGGCGGGCAGGGGAGAGCCCGAGAGTCGATCTATACTACGGATCAAGCGAGGCTGAGG
I  I  S  C  S  G  T  S  S  N  I  G  G  N  S  Y  N  W  Y  Q  H  P  P  G  A  A  P  R  L  L  I  Y  T  T  D  Q  R  P  S  G
                CDR1                                                                              CDR2
              (SEQ ID NO:56)                                                                  (SEQ ID NO:57)
      370       380       390       400       410       420       430       440       450       460       470       480
GGTCCCTGAACGGATTCTCTGGCTCGAAGTCTGGGACCTCTGCCTCCCTGGCCATCAGTGGACTCCAATCTGAGGATGAGGCTGATGAGTGTGGAATTTGGAGTTGGAATGAGAGCGTGACTCG
V  P  D  R  F  S  G  S  K  S  G  T  S  A  S  L  A  I  S  G  L  Q  S  E  D  E  A  D  Y  Y  G  E  V  W  D  D  S  L  I  R
                                                                                                    CDR3
                                                                                                (SEQ ID NO:58)
      490       500       510       520       530       540       550       560       570       580       590       600
TCCGGTGTTCGGCGAGGGAGCCGACCAAGGTTGACGGTCGTAGGTCAGCCGCAAAGGCTGCCCCGTCGGTCACTCTGTTCCCGCCCTCTCTGAGGAGCTTGAAGGCCAACAAGGCCACAGCTGGTTGTG
P  V  F  G  G  G  T  K  L  T  V  L  R  Q  P  K  A  A  P  S  V  T  L  F  P  P  S  S  E  E  L  Q  A  N  K  A  T  L  V  C
                                        CL1
      610       620       630       640       650       660       670       680       690       700       710       720
TCTCATAAGTGACTTCTACCCGGGAGCCGTGACCGTGAAGGCGGATGATCGGAAAGCAGATAGGAGGCGGGAGTGGAAGGCGACCAGCAGCCCGGTCAAAGAAGCAGACAGCAAGAAGACAAGTACGGGGC
L  I  S  D  F  Y  P  G  A  V  T  V  A  W  K  A  D  S  S  P  V  K  A  G  V  E  T  T  T  P  S  K  Q  S  N  N  K  Y  A  A
      730       740       750       760       770       780       790       800       810       820
CAGGAGGTACGTTGAGCGGTGAGCCTGAGCCGGTGCCAGTCCCAACAAAAAGGTACCAAGTCAGCGATGAAGACGACTGGTGGAACTTCAGCAGTACAAGTGAGAAGACTGG
S  S  Y  L  S  L  T  P  E  Q  W  K  S  H  K  S  Y  S  C  Q  V  T  H  E  E  S  T  V  E  K  T  M  (SEQ ID NO:84)
```

Figure 13

```
              167         173 - 181 (SEQ ID NO:1)       187
       T M P N N D N F D K L Y I W G V H H P S T    (SEQ ID NO:59)
Ai/68                                                (SEQ ID NO:59)
Gz/89  . . . . . . . G K . . . . . . . . I . . .    (SEQ ID NO:60)
Wy/03  . . . . . . . E K . . . . . . . . V . . .    (SEQ ID NO:61)
NY/04  . . . . . . . E K . . . . . . . . V . . .    (SEQ ID NO:62)
Hi/05  . . . . . . . E K . . . . . . . . G . . .
                              (SEQ ID NO:2)

225      227 - 239 (SEQ ID NO:3)     241
       G L S S R I S I Y W T I V K P G D
Ai/68                                              (SEQ ID NO:63)
Gz/89  . . . . . . . . . . . . . . . . .           (SEQ ID NO:64)
Wy/03  . . D I . . . . . . . . . . . P . .         (SEQ ID NO:65)
NY/04  . . D I . . . . . . . . . . . P . .         (SEQ ID NO:66)
Hi/05  . . N I . . . . . . . . . . . P . .
                        (SEQ ID NO:4)
```

Figure 14

LOCATIONS OF PEPTIDE CHAINS RECOGNIZED BY B-1 AND D-1 MONOCLONAL ANTIBODIES IN CONFORMATIONAL STRUCTURE OF HA1 REGION OF HUMAN INFLUENZA A VIRUS SUBTYPE H3N2.

Figure 15

COMPARISON OF PEPTIDE CHAINS RECOGNIZED BY B-1 AND D-1 WITH EPITOPES IN DATABASE

```
A.Aichi.2.1968.prj      121:ITEGFTWTGVTQNGGSNACKRGPGSGFFSR

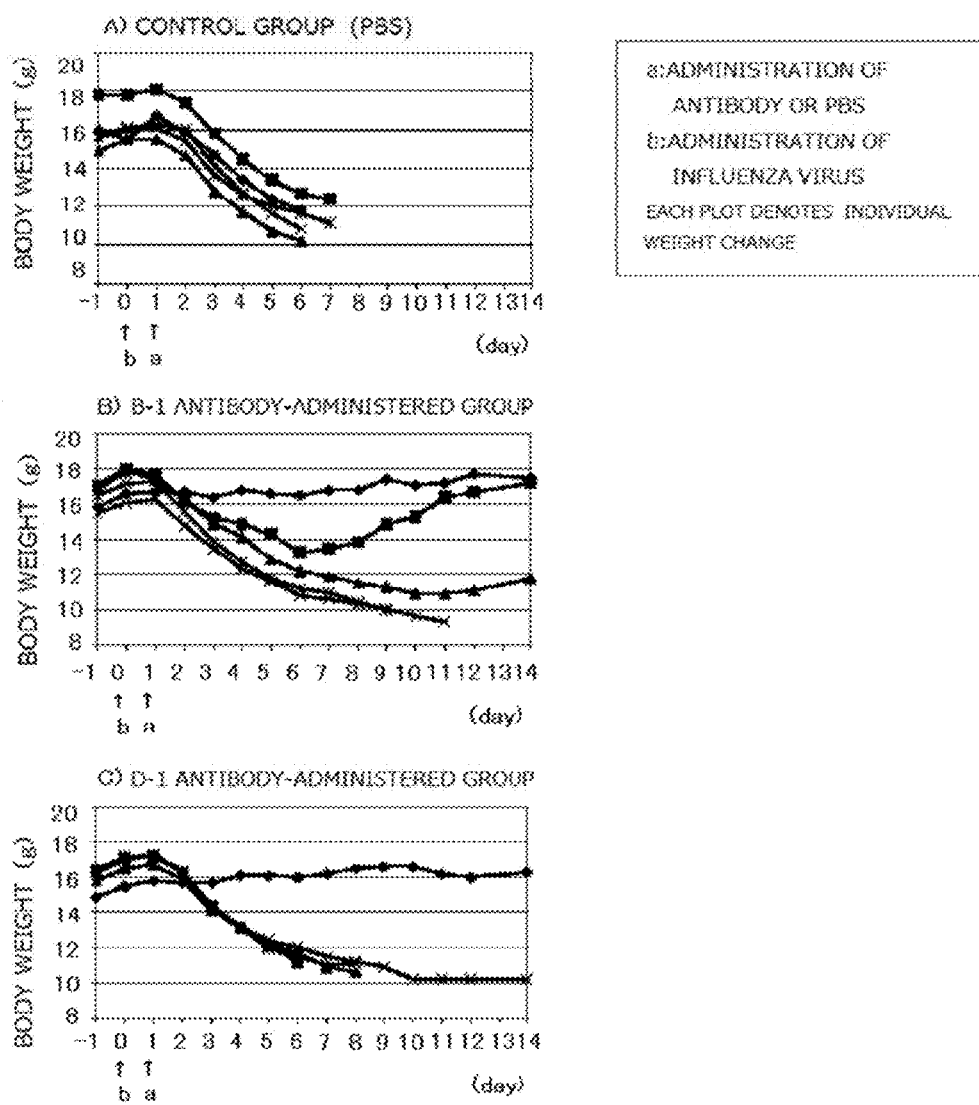

HUMAN ANTI-HUMAN INFLUENZA VIRUS ANTIBODY

TECHNICAL FIELD

The present invention relates to a human anti-human influenza virus antibody, which has a neutralization activity against a human influenza A virus subtype H3N2 and binds to a hemagglutinin HA1 region of the human influenza A virus subtype H3N2, or which has a neutralization activity against a human influenza B virus.

The present application is a continuation application of U.S. patent application Ser. No. 13/141,998, filed Jun. 24, 2011, which is a National Stage Application of PCT/JP2009/007159, filed Dec. 24, 2009, which claims priority of Japanese Patent Application No. 2008-330425, filed Dec. 25, 2008, and Japanese Patent Application No. 2009-146832, filed Jun. 19, 2009, which are incorporated herein by reference.

BACKGROUND ART

Influenza viruses belong to the Orthomyxoviridae family and are classified into three genera of types A, B, and C, which are referred to as influenza A virus, influenza B virus, and influenza C virus, respectively. In general, the influenza virus often refers to the types A and B in particular. Differences among types A, B, and C are based on differences in antigenicity of an M1 protein and an NP protein among proteins which form viral particles. Further, even though the influenza virus is classified into the same types A and B, each of the types is further classified into several subtypes or strains due to a difference in antigenicity of hemagglutinin (hereinafter, also referred to as "HA" simply) which is a molecule on the surface of an envelope or a difference in antigenicity of neuraminidase (NA). Thus, for example, the influenza A virus is further classified into subtypes H1N1, H2N2, H3N2, and the like. The human influenza A virus periodically mutates HA and NA. Thus, vaccination corresponding to the conventional subtype often cannot exert its expected effect.

HA in the influenza A virus is formed of a head region and a stem region which are different in structure, the head region includes a receptor-binding site for the virus to bind to a target cell and is involved in hemagglutination activity of HA, and the stem region includes a fusion peptide required for membrane fusion between the envelope of the virus and an endosome membrane of a cell and is involved in fusion activity (Non Patent Literature 1). Most of anti-HA antibodies, which recognize each of the influenza A virus subtypes H1N1 and H2N2, recognize the head region of HA. However, this region is most frequently mutated. Thus, these antibodies do not react with the subtypes of the human influenza A virus in common, and often lose their recognition abilities along with an antigenic change of HA in the virus.

Patent Literature 1 and Non Patent Literature 2 disclose that a polypeptide was synthesized from the amino acid sequence of the stem region of HA from one type of the influenza A virus subtype H3N2 and an antibody against this polypeptide was acquired. However, a viral neutralization activity was weak in such antibody (Patent Literature 1), and the polypeptide itself used as an antigen exhibited no reactivity with rabbit anti-virus serum obtained by immunization with the subtype H3N2, which was also problematic in antigenicity (Non Patent Literature 2).

If an antibody which is common to the subtypes of the influenza virus, recognizes an antigenic site which is hardly mutated in, for example, the HA or NA molecule, and has a neutralization activity against the influenza virus can be obtained, this can be utilized for diagnosing, preventing, and treating a disease caused by an infection with the virus, and the antigenic site itself becomes useful as a vaccine. There is disclosed an antibody which has a viral neutralization activity against influenza A virus subtypes H1N1 and H2N2 and exhibits no neutralization activity against the subtype H3N2 (Patent Literatures 2 and 3). There is also disclosed an antibody which recognizes a specific polypeptide sequence in the stem region of the influenza A virus subtype H3N2 and does not recognize the subtypes H1N1 and H2N2 (Patent Literature 4). There is also disclosed a human Fab antibody which neutralizes the influenza A virus subtype H3N2 (Patent Literature 5 and Non Patent Literature 3).

In the influenza viruses, the human influenza A virus causes worldwide epidemics and brings many deaths (Patent Literatures 2 to 4). The influenza A virus subtype H3N2 is a subtype which caused worldwide epidemics in the past, and there is a report that a strain resistant to a medicament such as amantadine having an anti-influenza virus action has been increasing in recent years (New York Times, Jan. 15, 2006). However, no report is available for an antibody which effectively exhibits a neutralization activity against a region highly conserved for about 20 years in the influenza A virus subtype H3N2 and in the influenza B virus.

CITATION LIST

Patent Literature

[PTL 1] JP 59-501714 A
[PTL 2] JP 06-100594 A
[PTL 3] JP 07-265077 A
[PTL 4] JP 07-304799 A
[PTL 5] JP 2006-254777 A

Non Patent Literature

[NPL 1] Rev. Biochem., 56, 365-394 (1987)
[NPL 2] Cell, 28, 477-487 (1982)
[NPL 3] Microbiol. Immunol., 52, 162-170 (2008)

SUMMARY OF INVENTION

Technical Problem

It is an object of the present invention to provide a human antibody having a neutralization activity against a human influenza virus. More particularly, it is the object of the present invention to provide a human antibody which recognizes a highly conserved region in a human influenza A virus subtype H3N2 or a human influenza B virus and has a neutralization activity against the virus.

Solution to Problem

As a result of an extensive study for solving the above-mentioned problems, the inventors of the present invention have achieved the production of a human anti-human influenza virus antibody by making a hybridoma from a peripheral blood mononuclear cell collected from a healthy donor vaccinated with an influenza vaccine and a cell capable of fusing with a human-derived lymphocyte with high efficiency, and selecting a cell producing an antibody which has a binding activity to an influenza virus-derived protein. The inventors have obtained an antibody of the present invention by selecting a human antibody which recognizes a highly conserved region particularly in a human influenza A virus subtype H3N2 or a human influenza B virus and has a neutralization activity against the virus, from the obtained antibodies.

That is, the present invention includes the following.

1. A human anti-human influenza virus antibody, which has a neutralization activity against a human influenza A virus subtype H3N2 and binds to a hemagglutinin HA1 region of the human influenza A virus subtype H3N2, or which has a neutralization activity against a human influenza B virus.

2. A human anti-human influenza virus antibody according to the item 1, in which the human anti-human influenza virus antibody is free of a neutralization activity against human influenza A virus subtypes H1 and H2.

3. A human anti-human influenza virus antibody according to the item 1, in which the human anti-human influenza virus antibody, which has a neutralization activity against a human influenza A virus subtype H3N2, has a neutralization activity against at least an A/Hiroshima/52/05 strain, and in which the human anti-human influenza virus antibody, which has a neutralization activity against a human influenza B virus, has a neutralization activity against at least a B/Malaysia/2506/04 strain.

4. A human anti-human influenza virus antibody according to any one of the items 1 to 3, in which an epitope recognized by the antibody includes a region including an amino acid sequence at positions 173 to 181 and/or a region including an amino acid sequence at positions 227 to 239 counting from an N-terminus of an amino acid sequence which forms the hemagglutinin HA1 region of the human influenza A virus subtype H3N2.

5. A human anti-human influenza virus antibody according to the item 4, in which the epitope includes an amino acid sequence including an amino acid sequence set forth in SEQ ID NO: 1 or 2, or any of amino acid sequences having substitutions, deletions, additions, or insertions of one or two amino acids in the amino acid sequence:

```
1)
                                              (SEQ ID NO: 1)
    NFDKLYIWG;
    and 2)
                                              (SEQ ID NO: 2)
    KFDKLYIWG.
```

6. A human anti-human influenza virus antibody according to the item 4, in which the epitope includes an amino acid sequence including an amino acid sequence set forth in SEQ ID NO: 3 or 4, or any of amino acid sequences having substitutions, deletions, additions, or insertions of one or two amino acids in the amino acid sequence:

```
1)
                                              (SEQ ID NO: 3)
    SSRISIYWTIVKP;
    and 2)
                                              (SEQ ID NO: 4)
    PSRISIYWTIVKP.
```

7. A human anti-human influenza virus antibody, including a base sequence of a DNA encoding a variable region of the antibody, the base sequence being selected from a base sequence set forth in any one of SEQ ID NOS: 5 to 12, or including any one of base sequences having substitutions, deletions, additions, or insertions of one or more nucleotides in the base sequence:

```
1)
                                                              (SEQ ID NO: 5)
GAGGAGAACCTGTTGCAGTCTGGGGGAGGCTTGGTCCAGCCGGGGGGTCCCTGAGACTCTC

CTGTGCAGGCTCTGGATTCACGTTTAGTACTTACGCCATGACCTGGGTCCGCCAGGCTCCAG

GACAGGGGCTGGAGTGGGTCTCCTCTATTAGCGGTAGTGGTGAAATTTCCTATTACGCAGAC

TCCGTGAAGGGCCTGTTCACCATCTCCAGGGACAATTCCAAGGACACAGTGTTTCTGCAAAT

GACCAGCCTGAGAGCCGAAGCACGGCCGTATATTACTGTGCGAAATCCGACGTTTGGGAGG

GTTATCGACCCTCAAAAGATGCTCTTCATATGTGGGGCCAAGGGACAATGGTCACCGTCTCT

TCA;

2)
                                                              (SEQ ID NO: 6)
GACGTCCAGATGACTCAGTCTCCATCCTCCCTGTCTGCATCTGTGGGAGACAGAGTCACCAT

CACTTGTCGGGCAAGTCAGAGCGTGAGCAATTATGTGAATTGGTATCAACAGAAGCCAGGGA

GAGCCCCTAGGCTCCTCATCTCTAGTGCGTCCAATTTGTGGGCTGGGGTCCCGCCAAGGTTC

AGTGGCCGTGGAGAAGAGACAGACTTCACTCTCACCATCACCAGTCTGCAACCTGAAGATTC

TGCAGTTTACTACTGTCAACAGAGTTACAGTGACCTTCTCAGTTTCGGCGGAGGGACCAAGG

TGGAGATCAAA;

3)
                                                              (SEQ ID NO: 7)
CAGGTGCAGCTGGTGCAATCTGGGTCTGAGTTGAAGAAGCCTGGGGCCTCAGTGAAGGTTTC

CTGCAAGGCTTCTGGATACACCTTCACCTCTTATTCTATATATTGGGTGCGACAGGCCCCTG
```

-continued

GACAAGGGCTTGAGTGGATGGGATGGATCAACACCAACACTGGGAACCCAAGCTATGCCCAG

GGCTTCACAGGACGGTTTGTCTTCTCCTTCGACACCTCTGTCAGCACGGCATATCTGGAGAT

CAGCAGCCTAAAGGCTGAGGACACTGCCGTGTATTACTGTGCGAGAGAGGGAGATTACGATA

TTTTGACTGGTTATTATTATTACTTTGACTACTGGGGCCAGGGAACCCTGGTCACCGTCTCC

TCA;

4)
(SEQ ID NO: 8)
CAGACTGTGGTGACCCAGGAGCCATCGTTCTCAGTGTCCCCTGGAGGGACAGTCACACTCAC

TTGTGGCTTGAGCTCTGGCTCAGTCTCTCCTAGTTACTACGCCAGCTGGTACCAGCAGACCC

CAGGCCAGGCTCCACGCACGCTCATCTACAACACAAACACTCGCTCCTCTGGGGTCCCTGAT

CGCTTCTCTGGCTCCTTCCTTGGGAGCGACGCTGCCCTCACCATCACGGGGGCCCAGGCAGA

TGATGAGTCTGATTATTTCTGTGTGCTGTATATGCCTAGTGGCGATTGGGTTTTCGGCGGAG

GGACCAAGCTGACCGTCCTAGGT;

5)
(SEQ ID NO: 9)
CAGGTGCAGTTGCAGGAGTCGGGCCCAGGACTGGTGAAGCCTTTACAGACCCTGTCCCTCAC

CTGCGTTGTCTCTGGTGACTCCATCAGCAGGGGTGGTTACTACTGGAGTTGGGTCCGCCAGC

CCCCAGAGAGGGGCCTGGAGTGGATTGGGGACATCTATCACAGTGGGAGTACCAACTACAAC

CCGGCCCTCAAGAGTCGAACTACCATCTCAGTAGAGACGTCCAAGAACCAGTTCTCCCTGCA

GCTGAACTCTGTGACCGCCGCAGACACGGCCGTGTATTACTGTGCCAGAGAGCCTCCACCTG

ACTACAGTGACTACAAGGTTGGGAAGGGTTATTTTGACTACTGGGGCCAGGGAGCCCTGGTC

ACCGTCTCCTCA;

6)
(SEQ ID NO: 10)
GAAATTGTGTTGGCACAGTCTCCAGCCACCCTGTCTTTGTCTCCAGGGGAAAGAGCCACCCT

CTCCTGCAGGGCCAGTGAGACCGTTGACACCTACTTAGCCTGGTACCAACAGAAACCTGGCC

AGGCTCCCAGGCTCCTCATAAATGATGCATCCAAGAGGGCCACTGGCATCCCAGCCAGGTTC

AGTGGCAGTGGGTCTGGGACAGACTTCACTCTCACCATCAGCGGCCTAGAGCCTGAAGATTT

TGCAGTTTATTGGTGTCAGCAGCATAGCAACTGGCCCCCCACCTTCGGCCAAGGGTCACGGC

TGGAGATTAAA;

7)
(SEQ ID NO: 11)
CAGGTGAAGTTGGTGCAGTCTGGCGGAGGCGCAGTCCAGCCTGGGAGGTCCCTGAGACTCTC

CTGTGAGGCGTCTGGATTCGACTTCACTGTGTATGACATCCACTGGGTCCGCCAGGCTCCAG

GCAAGGGGCTTGAGTGGGTGGCATCTATTTGGCATAACGGAGGAAAAGCATATTATGCGGAC

TCCGTGAAGGGCCGATTCACCGTGTCCAGAGACAATCCCCAGAAGACAGTGTATCTGCAAAT

GAGTGGCCTGAGACCCGAGGACACGGCTACATATTACTGTGCGAGAGAGTTTCCTTTCATGG

GCATCTATGACTACGGCATGGACGCCTGGGGCCAAGGGACCACGGTCACCGTCGCCTCA;
and 8)
(SEQ ID NO: 12)
CAGTCTGTGCTGGCTCAGCCACCCTCAGCGTCTGGGACCCCCGGGCAGAGGGTCATCATCTC

TTGTTCTGGAACCTCCTCCAACATCGGCGGTAATTCTGTCAACTGGTACCAGCACCCCCCAG

GGGCGGCCCCGAGACTCCTCATCTATACTACCGATCAGCGACCCTCAGGGGTCCCTGACCGA

TTCTCTGGCTCCAAGTCTGGCACCTCTGCCTCCCTGGCCATCAGTGGGCTCCAATCTGAGGA

-continued

```
TGAGGCTGATTATTACTGTGAAGTTTGGGATGACAGCCTGACTCGTCCGGTGTTCGGCGGAG

GGACCAAGTTGACCGTCCTACGT.
```

8. A human anti-human influenza virus antibody according to the item 7, in which an antigen of the human anti-human influenza virus antibody is a human influenza virus A/Hiroshima/52/05 strain or B/Malaysia/2506/04 strain.

9. A human anti-human influenza virus antibody according to the item 7, in which the antibody having a variable region encoded by DNA set forth in any one of SEQ ID NOS: 5 to 8 among the DNAs each encoding a variable region of the antibody includes an antibody having a neutralization activity against a human influenza A virus subtype H3N2, and in which the antibody having a variable region encoded by DNA set forth in any one of SEQ ID NOS: 9 to 12 includes a neutralization activity against a human influenza B virus.

10. A human anti-human influenza virus antibody according to the item 8, in which the DNA set forth in any one of SEQ ID NOS: 5, 7, 9 and 11 among the DNAs each encoding a variable region of the antibody includes a DNA encoding a heavy chain variable region, and the DNA set forth in any one of SEQ ID NOS: 6, 8, 10, and 12 includes a DNA encoding a light chain variable region.

11. A human anti-human influenza virus antibody according to any one of the items 1 to 11, in which the antibody includes an intact antibody.

12. A DNA, which encodes a variable region of the human anti-human influenza virus antibody according to any one of the items 1 to 11, the DNA including a polynucleotide which is selected from a base sequence set forth in any one of SEQ ID NOS: 5 to 12 or which includes any one of base sequences having substitutions, deletions, additions, or insertions of one or more nucleotides in the base sequence:

```
1)
                                                  (SEQ ID NO: 5)
GAGGAGAACCTGTTGCAGTCTGGGGGAGGCTTGGTCCAGCCGGGGGGGTCCCTGAGACTCTC

CTGTGCAGGCTCTGGATTCACGTTTAGTACTTACGCCATGACCTGGGTCCGCCAGGCTCCAG

GACAGGGGCTGGAGTGGGTCTCCTCTATTAGCGGTAGTGGTGAAATTTCCTATTACGCAGAC

TCCGTGAAGGGCCTGTTCACCATCTCCAGGGACAATTCCAAGGACACAGTGTTTCTGCAAAT

GACCAGCCTGAGAGCCGAAGACACGGCCGTATATTACTGTGCGAAATCCGACGTTTGGGAGG

GTTATCGACCCTCAAAAGATGCTCTTCATATGTGGGGCCAAGGGACAATGGTCACCGTCTCT

TCA;

2)
                                                  (SEQ ID NO: 6)
GACGTCCAGATGACTCAGTCTCCATCCTCCCTGTCTGCATCTGTGGGAGACAGAGTCACCAT

CACTTGTCGGGCAAGTCAGAGCGTGAGCAATTATGTGAATTGGTATCAACAGAAGCCAGGGA

GAGCCCCTAGGCTCCTCATCTCTAGTGCGTCCAATTTGTGGGCTGGGGTCCCGCCAAGGTTC

AGTGGCCGTGGAGAAGAGACAGACTTCACTCTCACCATCACCAGTCTGCAACCTGAAGATTC

TGCAGTTTACTACTGTCAACAGAGTTACAGTGACCTTCTCAGTTTCGGCGGAGGGACCAAGG

TGGAGATCAAA;

3)
                                                  (SEQ ID NO: 7)
CAGGTGCAGCTGGTGCAATCTGGGTCTGAGTTGAAGAAGCCTGGGGCCTCAGTGAAGGTTTC

CTGCAAGGCTTCTGGATACACCTTCACCTCTTATTCTATATATTGGGTGCGACAGGCCCCTG

GACAAGGGCTTGAGTGGATGGGATGGATCAACACCAACACTGGGAACCCAAGCTATGCCCAG

GGCTTCACAGGACGGTTTGTCTTCTCCTTCGACACCTCTGTCAGCACGGCATATCTGGAGAT

CAGCAGCCTAAAGGCTGAGGACACTGCCGTGTATTACTGTGCGAGAGAGGGAGATTACGATA

TTTTGACTGGTTATTATTATTACTTTGACTACTGGGGCCAGGGAACCCTGGTCACCGTCTCC

TCA;

4)
                                                  (SEQ ID NO: 8)
CAGACTGTGGTGACCCAGGAGCCATCGTTCTCAGTGTCCCCTGGAGGGACAGTCACACTCAC

TTGTGGCTTGAGCTCTGGCTCAGTCTCTCCTAGTTACTACGCCAGCTGGTACCAGCAGACCC

CAGGCCAGGCTCCACGCACGCTCATCTACAACACAAACACTCGCTCCTCTGGGGTCCCTGAT

CGCTTCTCTGGCTCCTTCCTTGGGAGCGACGCTGCCCTCACCATCACGGGGGCCCAGGCAGA
```

-continued 5)
(SEQ ID NO: 9)
CAGGTGCAGTTGCAGGAGTCGGGCCCAGGACTGGTGAAGCCTTTACAGACCCTGTCCCTCAC

CTGCGTTGTCTCTGGTGACTCCATCAGCAGGGGTGGTTACTACTGGAGTTGGGTCCGCCAGC

CCCCAGAGAGGGGCCTGGAGTGGATTGGGGACATCTATCACAGTGGGAGTACCAACTACAAC

CCGGCCCTCAAGAGTCGAACTACCATCTCAGTAGAGACGTCCAAGAACCAGTTCTCCCTGCA

GCTGAACTCTGTGACCGCCGCAGACACGGCCGTGTATTACTGTGCCAGAGAGCCTCCACCTG

ACTACAGTGACTACAAGGTTGGGAAGGGTTATTTTGACTACTGGGGCCAGGGAGCCCTGGTC

ACCGTCTCCTCA;

6)
(SEQ ID NO: 10)
GAAATTGTGTTGGCACAGTCTCCAGCCACCCTGTCTTTGTCTCCAGGGGAAAGAGCCACCCT

CTCCTGCAGGGCCAGTGAGACCGTTGACACCTACTTAGCCTGGTACCAACAGAAACCTGGCC

AGGCTCCCAGGCTCCTCATAAATGATGCATCCAAGAGGGCCACTGGCATCCCAGCCAGGTTC

AGTGGCAGTGGGTCTGGGACAGACTTCACTCTCACCATCAGCGGCCTAGAGCCTGAAGATTT

TGCAGTTTATTGGTGTCAGCAGCATAGCAACTGGCCCCCCACCTTCGGCCAAGGGTCACGGC

TGGAGATTAAA;

7)
(SEQ ID NO: 11)
CAGGTGAAGTTGGTGCAGTCTGGCGGAGGCGCAGTCCAGCCTGGGAGGTCCCTGAGACTCTC

CTGTGAGGCGTCTGGATTCGACTTCACTGTGTATGACATCCACTGGGTCCGCCAGGCTCCAG

GCAAGGGGCTTGAGTGGGTGGCATCTATTTGGCATAACGGAGGAAAAGCATATTATGCGGAC

TCCGTGAAGGGCCGATTCACCGTGTCCAGAGACAATCCCCAGAAGACAGTGTATCTGCAAAT

GAGTGGCCTGAGACCCGAGGACACGGCTACATATTACTGTGCGAGAGAGTTTCCTTTCATGG

GCATCTATGACTACGGCATGGACGCCTGGGGCCAAGGGACCACGGTCACCGTCGCCTCA;
and 8)
(SEQ ID NO: 12)
CAGTCTGTGCTGGCTCAGCCACCCTCAGCGTCTGGGACCCCCGGGCAGAGGGTCATCATCTC

TTGTTCTGGAACCTCCTCCAACATCGGCGGTAATTCTGTCAACTGGTACCAGCACCCCCCAG

GGGCGGCCCCGAGACTCCTCATCTATACTACCGATCAGCGACCCTCAGGGGTCCCTGACCGA

TTCTCTGGCTCCAAGTCTGGCACCTCTGCCTCCCTGGCCATCAGTGGGCTCCAATCTGAGGA

TGAGGCTGATTATTACTGTGAAGTTTGGGATGACAGCCTGACTCGTCCGGTGTTCGGCGGAG

GGACCAAGTTGACCGTCCTACGT.

13. A composition, including the human anti-human influenza virus antibody according to any one of the items 1 to 11.

Advantageous Effects of Invention

The human anti-human influenza virus antibody of the present invention has a neutralization activity against a highly conserved region in each of the human influenza A virus subtype H3N2 and the human influenza B virus.

Specifically, in the antibodies of the present invention, the antibody against the human influenza A virus subtype H3N2 has a neutralization activity against at least a viral strain of an A/Hiroshima/52/05 strain (isolated in 2005), and the antibody against the human influenza B virus has a neutralization activity against at least a viral strain of a B/Malaysia/2506/04 strain (isolated in 2004). Further, the antibodies also have neutralization activities against influenza virus vaccine strains in various generations including: various viral strains from the human influenza A virus subtype H3N2, such as an A/Aichi/2/68 strain (isolated in 1968), an A/Guizhou/54/89 strain (isolated in 1989), an A/Wyoming/3/03 strain (isolated in 2003), an A/New York/55/04 strain (isolated in 2004), and an A/Hiroshima/52/05 strain (isolated in 2005); and various viral strains from the human influenza B virus, such as a B/Victoria/2/87 strain (isolated in 1987), a B/Malaysia/2506/04 strain (isolated in 2004), a B/Mie/1/93 strain (isolated in 1993), and a B/Shanghai/261/02 strain (isolated in 2002), respectively.

Further, when administered prophylactically or therapeutically in vivo, the antibody against the human influenza A virus subtype H3N2 of the present invention exhibits effects on a survival rate and a weight loss in at least an infection with the influenza virus A/Guizhou/54/89xA/PR/8/34 (H3N2) strain.

That is, the antibody against the human influenza A virus subtype H3N2 of the present invention has an activity against a region which has been conserved for about 20 years, and also includes one having an activity against a region which has been conserved for 40 years or more. The antibody against the human influenza B virus has an activity against a region which has been conserved for 20 years or more. Meanwhile, an HI (hemagglutination inhibition) activity in the antibody of the present invention is equal to or less than the detection limit.

BRIEF DESCRIPTION OF DRAWINGS

FIG. 2 are graphs showing the results of confirming a neutralization activity of each hybridoma culture supernatant against influenza virus vaccine strains in various generations (Experimental Example 1-4).

FIG. 4 is a view showing a sequence of a light chain variable region of the B-1 monoclonal antibody (Experimental Example 1-5).

FIG. 5 is a view showing a sequence of a heavy chain variable region of the D-1 monoclonal antibody (Experimental Example 1-5).

FIG. 8 is a view showing a sequence of a light chain variable region of the E-2 monoclonal antibody (Experimental Example 1-5).

FIG. 10 is a view showing a sequence of a light chain variable region of the B-3 monoclonal antibody (Experimental Example 1-5).

FIG. 13 is a view showing sequences of peptide chains (epitopes) recognized by the B-1 and D-1 monoclonal antibodies, respectively, in a hemagglutinin HA1 region of each influenza virus vaccine strain from a human influenza A virus subtype H3N2 (Experimental Example 1-8).

FIG. 14 is a view showing locations of the peptide chains recognized by the B-1 and D-1 monoclonal antibodies, respectively, in a conformational structure of the hemagglutinin HA1 region of the human influenza A virus subtype H3N2 (Experimental Example 1-8).

FIG. 15 is a view showing a comparison between the peptide chains recognized by the B-1 and D-1 monoclonal antibodies, respectively, and epitopes in a database (Example 1-8).

FIG. 19 are graphs showing body weight changes when each of the B-1 and -1 monoclonal antibodies is therapeutically administered to five mice. Each plot shows the body weight change of each mouse (Experimental Example 2-2).

DESCRIPTION OF EMBODIMENTS

Figure 1:
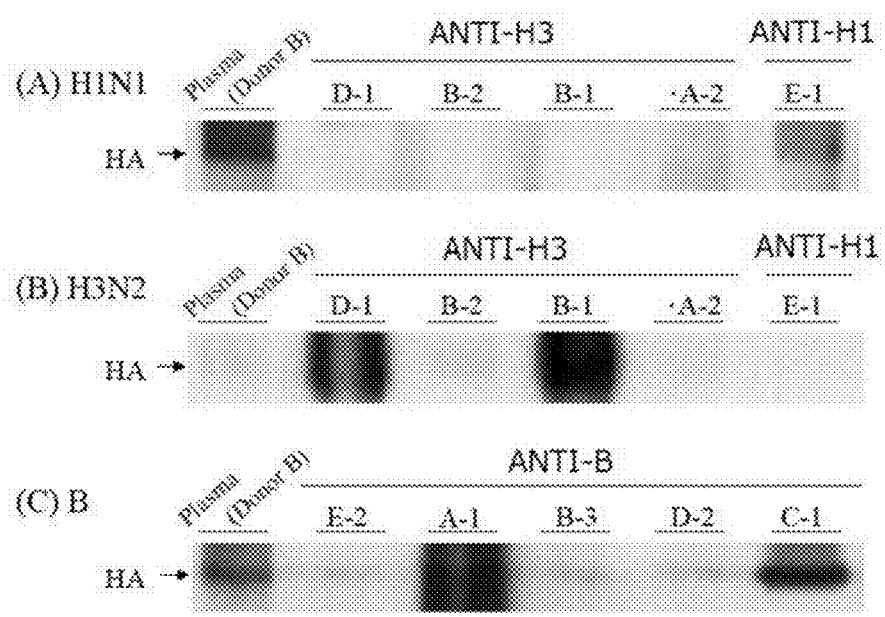
FIG. 1 are images showing the results of confirming reactivity of a culture supernatant of each hybridoma producing an A-1, A-2, B-1, B-2, B-3, C-1, D-1, D-2, E-1, or E-2 monoclonal antibody against HA of each influenza virus by western blotting assay (Experimental Example 1-2).
Figure 3:
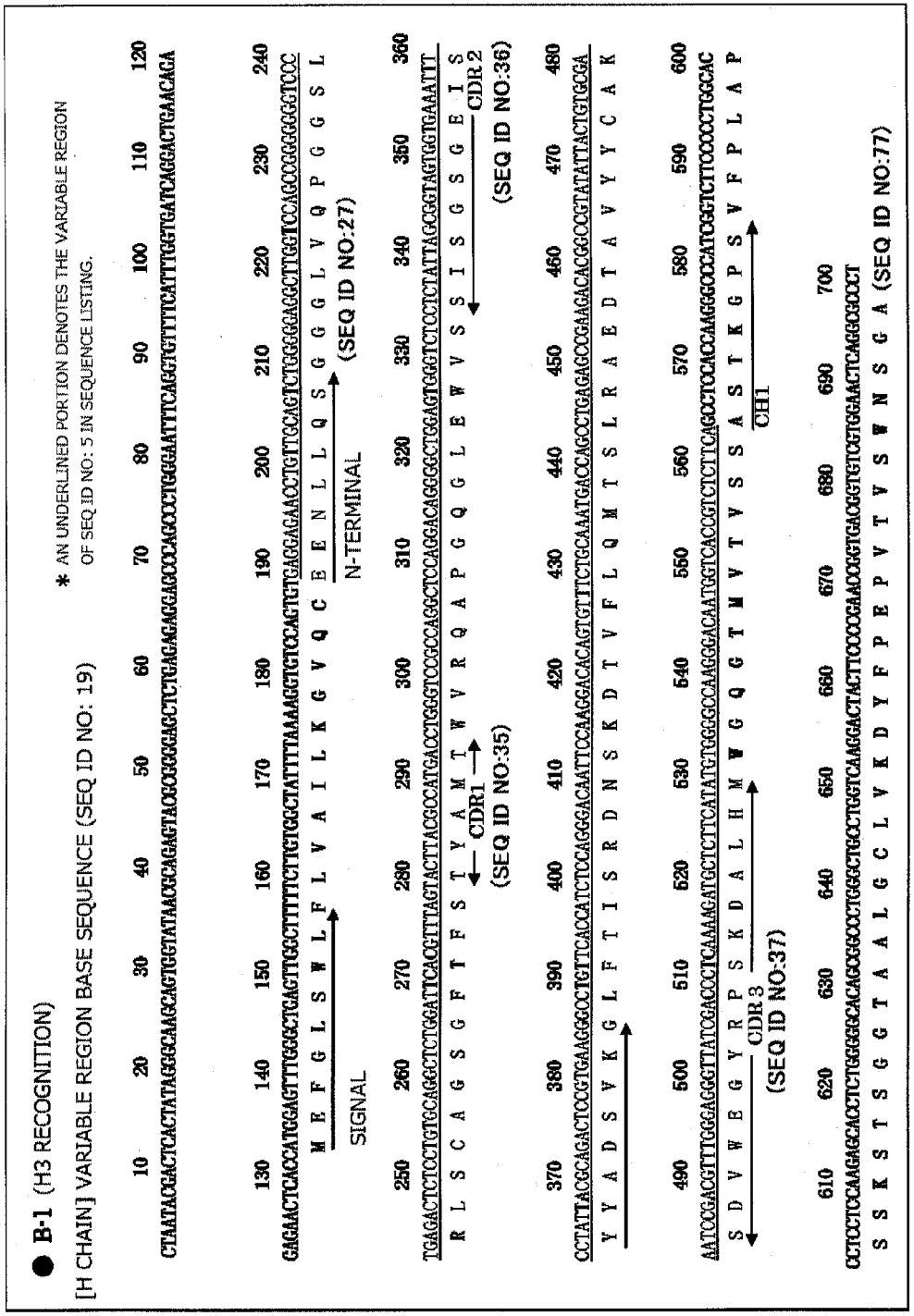
FIG. 3 is a view showing a sequence of a heavy chain variable region of the B-1 monoclonal antibody (Experimental Example 1-5).
Figure 6:
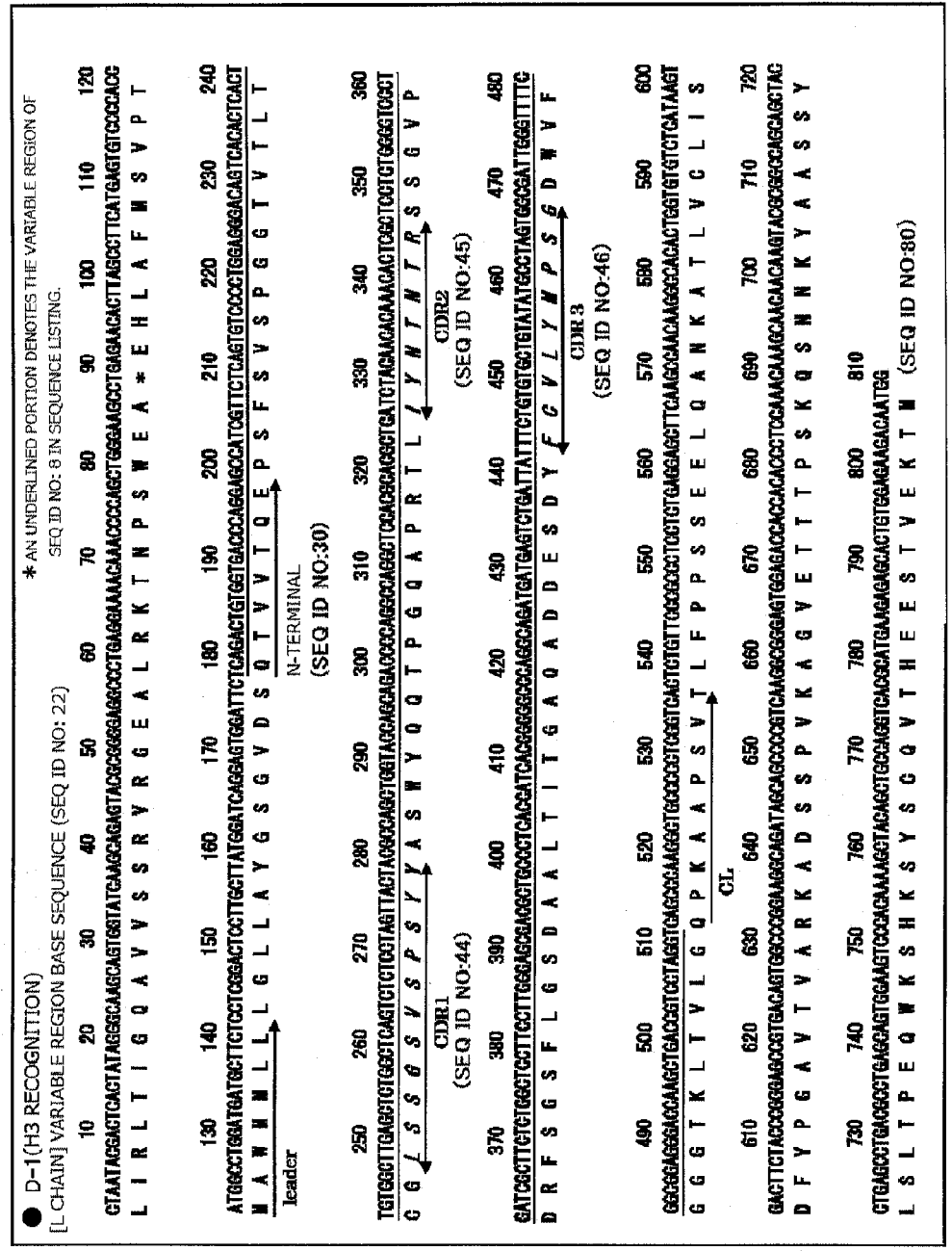
FIG. 6 is a view showing a sequence of a light chain variable region of the D-1 monoclonal antibody (Experimental Example 1-5).
Figure 7:
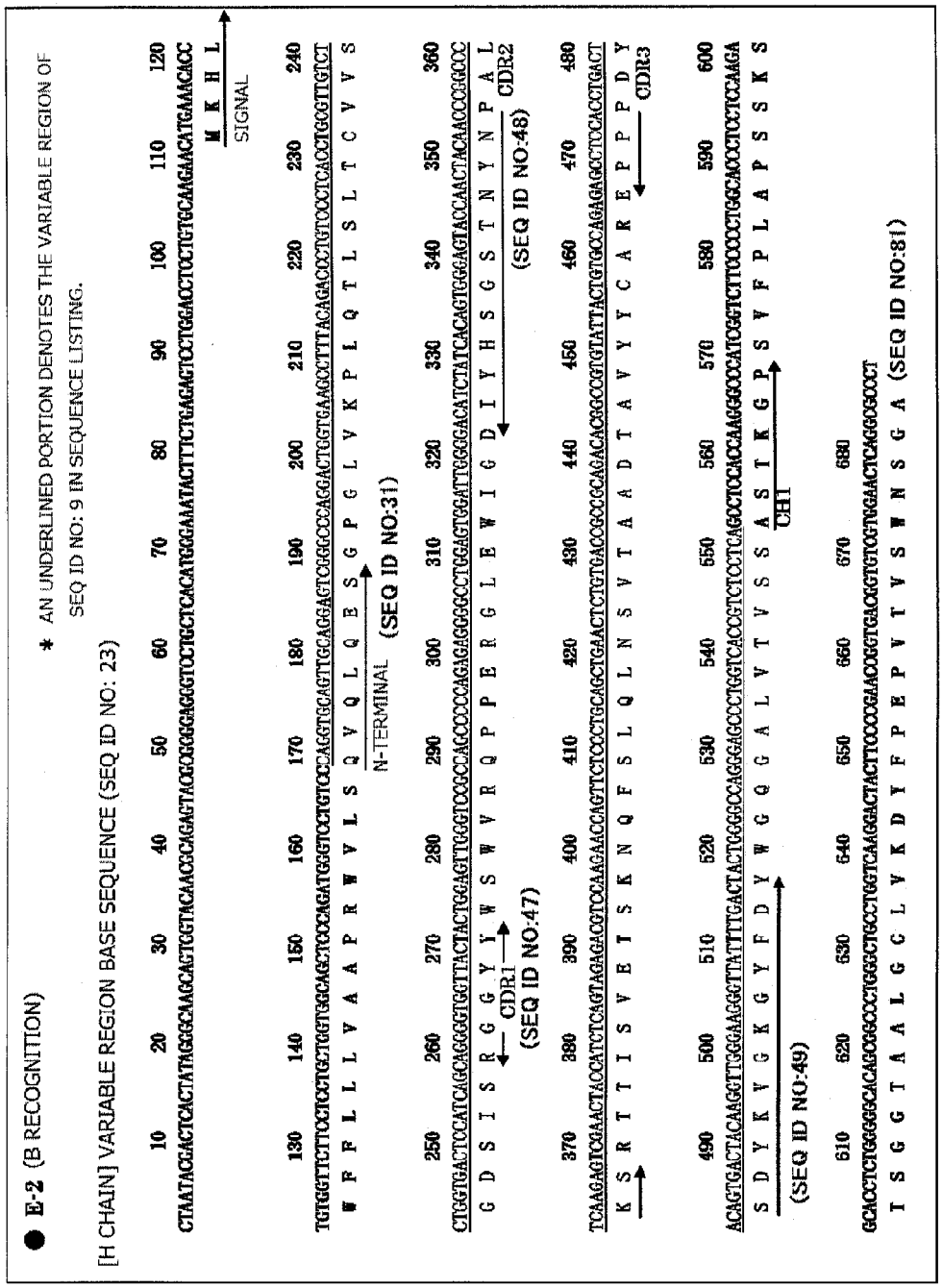
FIG. 7 is a view showing a sequence of a heavy chain variable region of the E-2 monoclonal antibody (Experimental Example 1-5).
Figure 9:
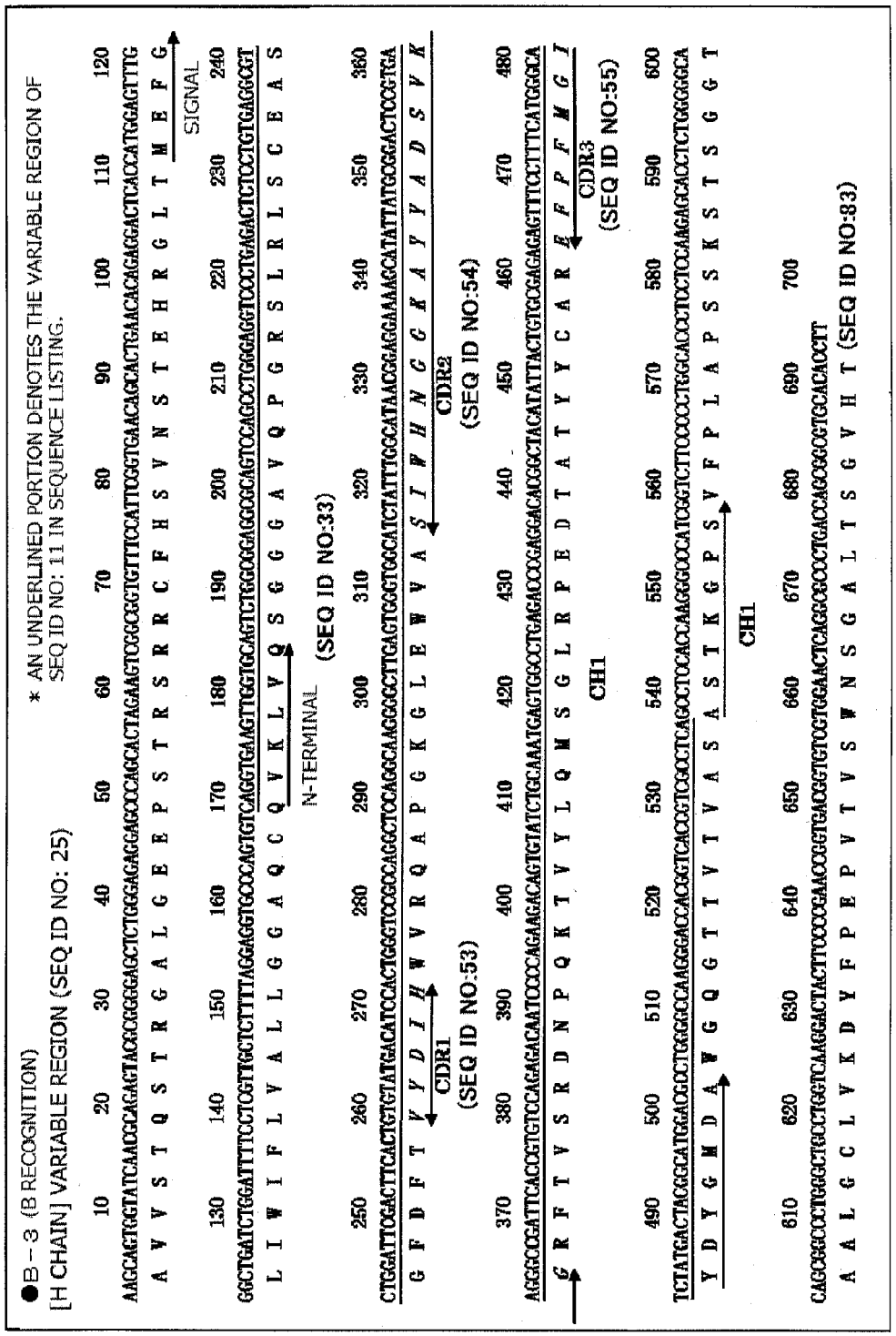
FIG. 9 is a view showing a sequence of a heavy chain variable region of the B-3 monoclonal antibody (Experimental Example 1-5).

The present invention relates to a human anti-human influenza virus antibody having the following properties (a) to (c):

(a) having a neutralization activity against a viral A/Hiroshima/52/05 strain (isolated in 2005) from the human influenza A virus subtype H3N2, or a neutralization activity against a viral B/Malaysia/2506/04 strain (isolated in 2004) from the human influenza B virus;

(b) having an HI (hemagglutination inhibition) activity equal to or less than the detection limit; and (c) having no neutralization activity against human influenza A virus subtypes H1N1 and H2N2.

The antibody of the present invention against the human influenza A virus subtype H3N2 has a neutralization activity against at least the A/Hiroshima/52/05 strain (isolated in 2005), and further, has neutralization activities against influenza virus vaccine strains in various generations including various viral strains from the human influenza A virus subtype H3N2, such as an A/Aichi/2/68 strain (isolated in 1968), an A/Guizhou/54/89 strain (isolated in 1989), an A/Wyoming/3/03 strain (isolated in 2003), and an A/New York/55/04 strain (isolated in 2004). Further, the antibody of the present invention against the human influenza B virus has a neutralization activity against at least the B/Malaysia/2506/04 strain (isolated in 2004), and further has neutralization activities against influenza virus vaccine strains in various generations including various virus strains derived from the human influenza B virus, such as a B/Victoria/2/87 strain (isolated in 1987), a B/Mie/1/93 strain (isolated in 1993), and a B/Shanghai/261/02 strain (isolated in 2002).

Among the antibodies of the present invention each having the above-mentioned properties, the antibody against the human influenza A virus subtype H3N2 recognizes a region including an amino acid sequence at positions 173 to 181 and/or a region including an amino acid sequence at positions 227 to 239 counting from the N-terminus of an amino acid sequence which forms the hemagglutinin HA1 region of the human influenza A virus. Here, the amino acid sequences which form the human influenza A virus subtype H3N2 are disclosed in GenBank Accession No. EU501660 for the A/Hiroshima/52/05 strain, in GenBank Accession No. D49963 for the A/Guizhou/54/89 strain, in GenBank Accession No. AY531033 for the A/Wyoming/3/03 strain, and in GenBank Accession No. EU501486 for the A/New York/55/04 strain.

The 227th amino acid counting from the N-terminus in the amino acid sequence which forms the hemagglutinin HA1 region of the human influenza A virus is serine (S) or proline (P), but such difference has no effect on the neutralization activity. The amino acid at that position is also S or P in the literature (Karoline et al Virology J. 2008, 5, 40). The variant at position 173 in the sequence is asparagine (N) or lysine (K), is K except in the A/Aichi strain isolated in 1968, and is K or glutamic acid (E) in the literature. Further, the 229th and 230th amino acids are different and are arginine (R) or glycine (G), and isoleucine (I) or valine (V), respectively, in the literature (Underwood, Mol. Immunol., 1987, 21, 7), and the 238th and 239th amino acids are different and are K or N, and P or R, respectively, in the sequences registered in GenBank.

In the light of the foregoing, a peptide chain (epitope) according to the region including an amino acid sequence at positions 173 to 181 is specifically an amino acid sequence including the amino acid sequence set forth in SEQ ID NO: 1 or 2, or is formed of an amino acid sequence in which one or two amino acids may be substituted, deleted, added or introduced in that sequence. A peptide chain (epitope) according to the region including an amino acid sequence at positions 227 to 239 is specifically an amino acid sequence including the amino acid sequence set forth in SEQ ID NO: 3 or 4, or is formed of an amino acid sequence in which one or two amino acids may be substituted, deleted, added, or introduced in that sequence.

1)
(SEQ ID NO: 1)
NFDKLYIWG 2)
(SEQ ID NO: 2)
KFDKLYIWG 3)
(SEQ ID NO: 3)
SSRISIYWTIVKP 4)
(SEQ ID NO: 4)
PSRISIYWTIVKP

Base sequences of DNAs encoding the variable region of the antibody of the present invention having the above-mentioned properties are specifically shown below.

A-1. Human Antibody (B-1) Against Human Influenza A Virus Subtype H3N2

Heavy chain variable region sequence:
(SEQ ID NO: 5)
GAGGAGAACCTGTTGCAGTCTGGGGGAGGCTTGGTCCAGCCGGGGGGGTCCCTGAGACTCTC

CTGTGCAGGCTCTGGATTCACGTTTAGTACTTACGCCATGACCTGGGTCCGCCAGGCTCCAG

GACAGGGGCTGGAGTGGGTCTCCTCTATTAGCGGTAGTGGTGAAATTTCCTATTACGCAGAC

TCCGTGAAGGGCCTGTTCACCATCTCCAGGGACAATTCCAAGGACACAGTGTTTCTGCAAAT

GACCAGCCTGAGAGCCGAAGACACGGCCGTATATTACTGTGCGAAATCCGACGTTTGGGAGG

GTTATCGACCCTCAAAAGATGCTCTTCATATGTGGGCCAAGGGACAATGGTCACCGTCTCT

TCA.

Light chain variable region sequence:
(SEQ ID NO: 6)
GACGTCCAGATGACTCAGTCTCCATCCTCCCTGTCTGCATCTGTGGGAGACAGAGTCACCAT

CACTTGTCGGGCAAGTCAGAGCGTGAGCAATTATGTGAATTGGTATCAACAGAAGCCAGGGA

GAGCCCCTAGGCTCCTCATCTCTAGTGCGTCCAATTTGTGGGCTGGGGTCCCGCCAAGGTTC

AGTGGCCGTGGAGAAGAGACAGACTTCACTCTCACCATCACCAGTCTGCAACCTGAAGATTC

TGCAGTTTACTACTGTCAACAGAGTTACAGTGACCTTCTCAGTTTCGGCGGAGGGACCAAGG

TGGAGATCAAA.

A-2. Human Antibody (D-1) Against Human Influenza A Virus Subtype H3N2

Heavy chain variable region sequence:
(SEQ ID NO: 7)
CAGGTGCAGCTGGTGCAATCTGGGTCTGAGTTGAAGAAGCCTGGGGCCTCAGTGAAGGTTTC

CTGCAAGGCTTCTGGATACACCTTCACCTCTTATTCTATATATTGGGTGCGACAGGCCCCTG

GACAAGGGCTTGAGTGGATGGGATGGATCAACACCAACACTGGGAACCCAAGCTATGCCCAG

GGCTTCACAGGACGGTTTGTCTTCTCCTTCGACACCTCTGTCAGCACGGCATATCTGGAGAT

CAGCAGCCTAAAGGCTGAGGACACTGCCGTGTATTACTGTGCGAGAGAGGGAGATTACGATA

-continued

```
TTTTGACTGGTTATTATTATTACTTTGACTACTGGGGCCAGGGAACCCTGGTCACCGTCTCC
TCA.
```

Light chain variable region sequence:
(SEQ ID NO: 8)
```
CAGACTGTGGTGACCCAGGAGCCATCGTTCTCAGTGTCCCCTGGAGGGACAGTCACACTCAC
TTGTGGCTTGAGCTCTGGCTCAGTCTCTCCTAGTTACTACGCCAGCTGGTACCAGCAGACCC
CAGGCCAGGCTCCACGCACGCTCATCTACAACACAAACACTCGCTCCTCTGGGGTCCCTGAT
CGCTTCTCTGGCTCCTTCCTTGGGAGCGACGCTGCCCTCACCATCACGGGGGCCCAGGCAGA
TGATGAGTCTGATTATTTCTGTGTGCTGTATATGCCTAGTGGCGATTGGGTTTTCGGCGGAG
GGACCAAGCTGACCGTCCTAGGT.
```

B-1. Human Antibody (E-2) Against Human Influenza B Virus

Heavy chain variable region sequence:
(SEQ ID NO: 9)
```
CAGGTGCAGTTGCAGGAGTCGGGCCCAGGACTGGTGAAGCCTTTACAGACCCTGTCCCTCAC
CTGCGTTGTCTCTGGTGACTCCATCAGCAGGGGTGGTTACTACTGGAGTTGGGTCCGCCAGC
CCCCAGAGAGGGGCCTGGAGTGGATTGGGGACATCTATCACAGTGGGAGTACCAACTACAAC
CCGGCCCTCAAGAGTCGAACTACCATCTCAGTAGAGACGTCCAAGAACCAGTTCTCCCTGCA
GCTGAACTCTGTGACCGCCGCAGACACGGCCGTGTATTACTGTGCCAGAGAGCCTCCACCTG
ACTACAGTGACTACAAGGTTGGGAAGGGTTATTTTGACTACTGGGGCCAGGGAGCCCTGGTC
ACCGTCTCCTCA.
```

Light chain variable region sequence:
(SEQ ID NO: 10)
```
GAAATTGTGTTGGCACAGTCTCCAGCCACCCTGTCTTTGTCTCCAGGGGAAAGAGCCACCCT
CTCCTGCAGGGCCAGTGAGACCGTTGACACCTACTTAGCCTGGTACCAACAGAAACCTGGCC
AGGCTCCCAGGCTCCTCATAAATGATGCATCCAAGAGGGCCACTGGCATCCCAGCCAGGTTC
AGTGGCAGTGGGTCTGGGACAGACTTCACTCTCACCATCAGCGGCCTAGAGCCTGAAGATTT
TGCAGTTTATTGGTGTCAGCAGCATAGCAACTGGCCCCCCACCTTCGGCCAAGGGTCACGGC
TGGAGATTAAA.
```

B-2. Human Antibody (B-3) Against Human Influenza B Virus

Heavy chain variable region sequence:
(SEQ ID NO: 11)
```
CAGGTGAAGTTGGTGCAGTCTGGCGGAGGCGCAGTCCAGCCTGGGAGGTCCCTGAGACTCTC
CTGTGAGGCGTCTGGATTCGACTTCACTGTGTATGACATCCACTGGGTCCGCCAGGCTCCAG
GCAAGGGGCTTGAGTGGGTGGCATCTATTTGGCATAACGGAGGAAAAGCATATTATGCGGAC
TCCGTGAAGGGCCGATTCACCGTGTCCAGAGACAATCCCCAGAAGACAGTGTATCTGCAAAT
GAGTGGCCTGAGACCCGAGGACACGGCTACATATTACTGTGCGAGAGAGTTTCCTTTCATGG
GCATCTATGACTACGGCATGGACGCCTGGGGCCAAGGGACCACGGTCACCGTCGCCTCA.
```

Light chain variable region sequence:
(SEQ ID NO: 12)
```
CAGTCTGTGCTGGCTCAGCCACCCTCAGCGTCTGGGACCCCCGGGCAGAGGGTCATCATCTC
TTGTTCTGGAACCTCCTCCAACATCGGCGGTAATTCTGTCAACTGGTACCAGCACCCCCCAG
GGGCGGCCCCGAGACTCCTCATCTATACTACCGATCAGCGACCCTCAGGGGTCCCTGACCGA
```

```
                           -continued
TTCTCTGGCTCCAAGTCTGGCACCTCTGCCTCCCTGGCCATCAGTGGGCTCCAATCTGAGGA

TGAGGCTGATTATTACTGTGAAGTTTGGGATGACAGCCTGACTCGTCCGGTGTTCGGCGGAG

GGACCAAGTTGACCGTCCTACGT.
```

The antibody of the present invention is not particularly limited as long as the antibody has the above-mentioned properties. For example, the base sequence encoding the variable region of the human antibody against the human influenza A virus subtype H3N2 is not limited to the base sequence set forth in any one of SEQ ID NOS: 5 to 8 described above, and may be a sequence in which one or more nucleotides are substituted, deleted, added or introduced in the above-mentioned sequence as long as the sequence has a neutralization ability against the human influenza A virus subtype H3N2. In an example of the substitution of one or more nucleotides, the base sequence may be varied due to, for example, codon degeneracy but has the neutralization ability. Preferably, the antibody having a neutralization ability against the human influenza A virus subtype H3N2 further recognizes any one of the peptide chains (epitopes) described above. Further, the base sequence encoding the variable region of the human antibody against the human influenza B virus is also not limited to the base sequence set forth in any one of SEQ ID NOS: 9 to 12 described above, and may be a sequence in which one or more nucleotides are substituted, deleted, added or introduced in the above-mentioned sequence as long as the sequence has a neutralization ability against the human influenza B virus. In an example of the substitution of one or more nucleotides, the base sequence may be varied different due to, for example, codon degeneracy but has the neutralization ability.

A monoclonal antibody obtained by a cell fusion method is typically derived from an immunized animal species, e.g., a mouse. A mouse antibody cannot exert its expected effect in a human because when administered to the human, the mouse antibody can be metabolized as foreign matter and thus the half-life of the mouse antibody is relatively short in the human. Further, a human anti-mouse antibody (HAMA) generated against the administered mouse antibody elicits an immune response such as serum disease or other allergy which is inconvenient and dangerous for a patient. Thus, medical and therapeutic values of the monoclonal antibody derived from another animal species are limited in a human. Therefore, when the monoclonal antibody is administered to a human as a pharmaceutical or the like, a human antibody is strongly desired.

A known method or any method to be developed in the future may be employed for a method of producing the human antibody. However, there is no standardized method capable of being universally applied to any human antibody, and various efforts are required for producing a human antibody which exhibits a sufficient binding activity and neutralization activity against a certain antigen. For example, reference can be made to Sato, K. et al, Cancer Res., 53, 851-856, 1993 and JP 2008-161198 A. The type of the human antibody is not particularly limited, and may be an Fab type or an intact type. The intact type antibody is desirable in order to effectively exert an antibody activity. The intact type antibody is not particularly limited, and can be an antibody in which a complementarity determining region (CDR) of the antibody is derived from an original animal species and a constant region (C region) is derived from an appropriate human. In such chimera antibody, the variable region including CDR of the antibody derived from an immunized animal is generally linked to the constant region of the human antibody. The chimera antibody can be easily constructed by genetic modification technology. A humanized antibody obtained by CDR grafting in which CDR of the antibody from the immunized animal species is grafted in the variable region of the human antibody may also be employed. The human antibody may have the human antibody having CDR derived from a human, and CDR derived from the immunized animal species in terms of antigenicity because amino acid substitutions frequently occur in the CDR region.

The human anti-human influenza virus antibody of the present invention having the above-mentioned properties (a) to (c) can be produced specifically by the following method. Peripheral blood mononuclear cells corresponding to 10 mL of blood are collected from a healthy donor 2 to 4 weeks after being vaccinated with an influenza vaccine. Hybridomas are made simply and efficiently by fusing the peripheral blood mononuclear cells with partner cells derived from a human, e.g., SPYMEG cells (manufactured by MBL) capable of highly efficient cell fusion with lymphocytes derived from a human by a method such as a polyethylene glycol method. A cell producing the antibody which has a binding activity to a protein derived from the influenza virus is selected from the hybridomas by an ELISA method in which a purified protein such as HA derived from the influenza virus is immobilized or a staining method using a cell infected with the influenza virus as an antigen, thereby enabling to produce the human anti-human influenza virus antibody.

As another method of producing the human antibody, for example, a so-called human combinatorial antibody library in which human antibody fragments are presented on the surface of *Escherichia coli* phage is constructed, and the desired human antibody can be obtained by screening of the antibodies with biopanning. In this case, the desired antibody can be screened without immunological work in an animal.

The present invention also encompasses a composition including the antibody of the present invention. Further, when used for medical usages, the composition of the present invention may include an effective amount of one or more kinds of human anti-human influenza virus antibodies of the present invention and further a pharmaceutically acceptable carrier. In the present invention, a pharmaceutically acceptable salt is exemplified by the following salts.

There are given as base addition salts: alkali metal salts such as a sodium salt and a potassium salt; alkaline earth metal salts such as a calcium salt and a magnesium salt; for example, an ammonium salt; aliphatic amine salts such as a trimethylamine salt, a triethylamine salt, a dicyclohexylamine salt, an ethanolamine salt, a diethanolamine salt, a triethanolamine salt, and a procaine salt; aralkylamine salts such as an N,N-dibenzylethylenediamine salt; heterocyclic aromatic amine salts such as a pyridine salt, a picoline salt, a quinoline salt, and an isoquinoline salt; quaternary ammonium salts such as a tetramethylammonium salt, a tetraethylammonium salt, a benzyltrimethylammonium salt, a benzyltriethylammonium salt, a benzyltributylammonium salt, a methyltrioctylammonium salt, and a tetrabutylammonium salt; basic amino acid salts such as an arginine salt and a lysine salt; and the like.

There are given as acid addition salts: inorganic acid salts such as a hydrochloric acid salt, a sulfuric acid salt, a nitric acid salt, a phosphoric acid salt, a carbonic acid salt, a hydrogen carbonate salt, and a perchloric acid salt; organic acid salts such as an acetic acid salt, a propionic acid salt, a lactic acid salt, a maleic acid salt, a fumaric acid salt, a tartaric acid salt, a malic acid salt, a citric acid salt, and an ascorbic acid salt; sulfonic acid salts such as a methanesulfonic acid salt, an isethionic acid salt, a benzenesulfonic acid salt, and a p-toluenesulfonic acid salt; acidic amino acid salts such as an aspartic acid salt and a glutamic acid salt; and the like.

Such composition can be orally or parenterally administered as a pharmaceutical composition. When administered orally, the human anti-human influenza virus antibody of the present invention can be used as any one of dosage forms such as: solids such as tablets, powders, granules, and capsules; aqueous solutions; oil suspensions; or solutions such as syrups or elixirs. When administered parenterally, the human anti-human influenza virus antibody of the present invention can be used as an aqueous or oil suspension for injection or a nasal solution. Commonly used excipients, binders, lubricants, aqueous solvents, oil solvents, emulsifiers, suspending agents, preservatives, stabilizers, and the like can be optionally used in its preparation.

EXAMPLES

To help understanding of the present invention, the present invention is specifically described below with reference to Examples and Experimental Examples, but it goes without saying that the present invention is not limited thereto.

Example 1

Preparation of Human Anti-Human Influenza Virus Antibody

In this example, a description is made of the preparation of a monoclonal antibody using a hybridoma.

1) Preparation of Viruses

Human influenza virus vaccine strains, i.e., A/New Caledonia/20/99 strain as A virus subtype H1N1, A/Hiroshima/52/05 strain as A virus subtype H3N2, and B/Malaysia/2506/04 strain as the human influenza B virus, given from National Institute of Infectious Diseases were each used to infect MDCK (canine kidney epithelial cell line) cells, which were then cultured at 37° C. in the presence of trypsin for 2 to 3 days, and then the virus was collected.

2) Purification of Influenza Virus HA Antigen

An influenza virus HA antigen was purified by a method well-known to those skilled in the art. The above-mentioned influenza virus vaccine strains were each inoculated to an incubated chicken egg, which was then cultured at 33 to 35° C. for 2 days and subsequently left stand overnight at 4° C., and then an infected allantoic fluid was collected. The fluid was then concentrated by ultrafiltration and the like, and viral particles were purified by a sucrose density gradient centrifugation method. That is, the fluid was ultracentrifuged at 35,000 rpm in 0 to 60% sucrose density gradient, and a fraction around 40% of the sucrose density gradient was collected. This concentrated viral fraction was treated with ether followed by adding formalin, and further purified by the sucrose density gradient centrifugation method to obtain the influenza HA antigen.

3) Preparation of Hybridoma 10 mL of peripheral blood were collected from a healthy donor 2 to 4 weeks after being vaccinated with an influenza vaccine prepared from a seasonal influenza vaccine in 2006/2007, specifically, an A/Hiroshima/52/05 strain as the human influenza A virus subtype H3N2 or a B/Malaysia/2506/04 strain as the human influenza B virus. A mononuclear cell fraction was collected using Ficoll Paque Plus (manufactured by GE Healthcare) to use as a cell fraction for producing hybridomas. The mononuclear cell fraction was washed with serum-free DMEM before cell fusion to obtain mononuclear cells as cells for preparing hybridomas. SPYMEG cells (manufactured by MBL) as hybrid myeloma cells of murine myeloma cells and human megakaryoblasts were used as partner cells for making hybridomas. The SPYMEG cells were cultured in a DMEM medium supplemented with 10% fetal bovine serum for 2 days after passage, and the resultant was washed with serum-free DMEM before cell fusion.

Subsequently, the mononuclear cells obtained in the foregoing and the SPYMEG cells were mixed at a ratio of 1:5 to 1:10, and centrifuged to remove a supernatant. The precipitated cell mass was loosened sufficiently, subsequently 0.6 mL of a 50% polyethylene glycol 1500-PBS solution was slowly added thereto with stirring over 1 minute, and then 10 mL of serum-free DMEM was slowly added thereto over 2 minutes. Further, 10 mL of serum-free DMEM were added followed by adding 1 mL of fetal bovine serum to complete the cell fusion. Subsequently, the resultant was centrifuged followed by removal of a supernatant, and the cells were washed with 20 mL of serum-free DMEM. Finally, the cells were gradually loosened, 120 mL of a hypoxanthine-aminopterin-thymidine (HAT) medium {HAT and additives for a human hybridoma medium, such as BM condimed (manufactured by Roche), were added to DMEM supplemented with 15% fetal bovine serum} were added thereto, and the cells were gradually suspended using a measuring pipette.

4) Cloning of Hybridoma

The cell suspension of the above-mentioned section 3) was dispensed in six 96-well microplates for culture, and cultured at 37° C. in an incubator containing 5% $CO_2$ for 10 to 14 days. A half amount of the HAT medium was changed every 3 to 4 days during this period. Subsequently, an aliquot of the culture supernatant was taken, and subjected to screening of the hybridomas.

The purified HA antigen (1 μg/well) prepared in the above-mentioned section 2) was immobilized on a 96-well microplate for ELISA, and further blocked with a PBS-0.1% Tween (TBS-T) solution of 5% defatted dry milk. Subsequently, 50 μL of the culture supernatant from the above-mentioned cultured cell suspension were added to each well of the microplate for ELISA, and reacted at 37° C. for 30 minutes to form a primary immune complex by the purified HA antigen and the anti-HA antigen antibody (human anti-human influenza virus antibody) on the solid phase in the well. The human anti-human influenza virus antibody in the culture supernatant was detected by reacting the primary immune complex with a peroxidase-labeled goat anti-antibody followed by peroxidase reaction with color development.

Cells contained in each well in the microplate for culture, in which cells were confirmed to produce the antibody and proliferated, were taken out, and limiting dilution for the cells was performed three times, and target cells were cloned by the same method as in the foregoing. The cloned hybridoma strains were designated as R1D8, K4E7, and G4G11.

5) Purification of Antibody

Each hybridoma strain was finally cultured in serum-free medium by reducing the content of the fetal bovine serum in the medium from 10% to 2%. 100 mL of each hybridoma culture supernatant obtained by culturing in the serum-free medium for 3 to 7 days were centrifuged at 2,000 rpm for 10 minutes, and the resulting supernatant was filtrated with a filter of 0.45 μm to remove solid contents. The filtrate was purified by 1 mL of 6% agarose gel having immobilized thereon Protein G (HiTrap Protein G HPTM manufactured by GE Healthcare). The monoclonal antibodies produced by the hybridoma strains R1D8, K4E7, and G4G11 were designated as B-1, D-1, and E-2, respectively. Likewise, monoclonal antibodies such as A-1, A-2, B-2, B-3, C-1, D-2, and E-1 were purified from other hybridoma supernatants.

Experimental Example 1-1

Characterization of Culture Supernatant of Each Hybridoma

1) Neutralization Activity

A neutralization activity of each hybridoma culture supernatant against each influenza virus was measured in accordance with Arch. Virol., 86, 129-135 (1985), Microbiol. Immunol., 29, 327-335 (1985).

MDCK cells were dispensed at $2 \times 10^4$ cells/well in a 96-well microplate (for measuring a neutralization activity), and cultured overnight at 37° C. An 8-fold diluted solution of each antibody culture supernatant from which non-specific inhibitors had been removed by RDE treatment and a viral solution obtained from the following influenza virus vaccine strain, each of which had been prepared so that a focus forming unit/well was 100, were mixed in equal amounts, and incubated at 37° C. for 1 hour. Subsequently, 30 μL of this mixture were dispensed in each well of the microplate, to which the cultured MDCK cells had been added, and incubated at 37° C. for 30 minutes. Subsequently, the solution in each well was removed, each well was washed with PBS, and fetal bovine serum-free MEM was added. The microplate was incubated at 37° C. for 6 to 10 hours. Then, the added solution was removed, and the cells were treated with absolute ethanol at room temperature for 10 minutes to fix the cells. Each well was dried, and the cells were stained by the same enzyme antibody staining method as the staining test. After being stained, the cells were washed with tap water, and after being dried, the number of stained foci was counted under an optical microscope. The neutralization activity was represented by a focus reduction rate. The results were shown in Table 1.

Human influenza virus vaccine strain:
A. Influenza A: A/New Calcdonia/20/99 strain (H1), A/Hiroshima/52/05 strain (H3N2)
B. Influenza B: B/Malaysia/2506/04 strain 2) Hemagglutination Inhibition Activity (HI) of Antibody 25 μL of serial dilution (2 to 64 times) of the hybridoma culture supernatant treated with RDE were added to each well of a 96-well microplate (for measuring a hemagglutination inhibition activity (HI)), then were mixed with 25 μL of each of the viruses (8 HA units/50 μL) used in the above-mentioned section 1), and reacted at room temperature for 30 minutes. Subsequently, 50 μL of 0.75% guinea pig erythrocytes were added and mixed thoroughly to examine the effect of the antibody in the hybridoma culture supernatant on the hemagglutination activity of each virus. The results were shown in Table 1.

TABLE 1

Human monoclonal antibodies against influenza virus

| HuMAb | ELISA[a] H1 H3 B | Staining of infected cells[b] H1 H3 B | Recognized virus type | HI activity[c] H1/H3/B | Neutralization activity (% inhibition)[c] H1/H3/B |
|---|---|---|---|---|---|
| A-1 | --+ | --+ | B | <2 | 0 |
| A-2 | -+- | -+- | AH3 | <2 | 4.3 |
| B-1 | -+- | -+- | AH3 | <2 | 98.9 |
| B-2 | -+- | -+- | AH3 | <2 | 0 |
| B-3 | --+ | --+ | B | <2 | 31.7 |
| C-1 | --+ | --+ | B | <2 | 0 |
| D-1 | -+- | -+- | AH3 | <2 | 80.5 |
| D-2 | --+ | --+ | B | <2 | 16.7 |
| E-1 | +-- | +-- | AH1 | <2 | 0 |
| E-2 | --+ | --+ | B | <2 | 37.8 |

[a]Antigenic virus for ELISA: virus vaccine antigens of H1: A/New Caledonia/20/99 strain, H3: A/Hiroshima/52/05 strain, and B: B/Malaysia/2506/04 strain
[b]Staining of infected cells: MDCX cells infected with H1: A/New Caledonia/20/99 strain, H3: A/Hiroshima/52/05 strain, or B: B/Malaysia/2506/04 strain and fixed with ethanol were used.
[c]HI activity with neutralization activity: activity againist any one of H1: A/New Caledonia/20/99 strain, H3: A/Hiroshima/52/05 strain, and B: B/Malaysia/2506/04 strain recognized by the antibody was shown.

As a result of examining the neutralization activity and HI activity of the culture supernatant of the hybridoma producing each monoclonal antibody against each influenza virus, it was confirmed that the culture supernatant of the hybridoma producing the B-1 or D-1 monoclonal antibody had a high neutralization activity against the human influenza A virus subtype H3N2, and that the culture supernatant of the hybridoma producing the B-3 or E-2 monoclonal antibody had a slightly high neutralization activity against the human influenza B virus. However, the HI activity was equal to or less than the detection limit in all of the culture supernatants.

Experimental Example 1-2

Confirmation of Binding of Hybridoma Culture Supernatant to HA of Each Virus by Western Blotting Western blotting assay of the culture supernatant of the hybridoma producing an A-1, A-2, B-1, B-2, B-3, C-1, D-1, D-2, E-1 or E-2 monoclonal antibody was performed for binding to HA of each virus. Plasma obtained from a patient with informed consent was used as a control. The purified HA antigen obtained in the section 2) of Example 1 was fractionated on SDS-PAGE, transferred onto a polyvinylidene fluoride (PVDF) membrane, and then blocked with a TBS-T solution of 5% defatted milk. The membrane was incubated with undiluted hybridoma culture supernatant or the plasma diluted to 2,000 folds with PBS-T at room temperature for 1 hour to perform an antigen antibody reaction. The blotted membrane was washed several times with PBS-T, and subsequently incubated in a solution containing a peroxidase-conjugated anti-human IgG antibody at room temperature for 1 hour. Development was performed with an ECL detection kit (manufactured by Amersham Biosciences).

As a result, it was confirmed that the culture supernatants of the hybridomas producing the D-1 and B-1 monoclonal antibodies each had a binding activity to HA of the human influenza A virus subtype H3N2, and that the culture supernatants of the hybridomas producing the A-1 and C-1 monoclonal antibodies each had a binding activity to HA of the human influenza B virus (FIG. 1).

Experimental Example 1-3

Staining Activity of Hybridoma Culture Supernatants in Cells Infected with Various Influenza Virus Vaccine Strains Staining activities in cells infected with the influenza virus vaccine strains in various generations shown below was examined for the supernatant of the hybridoma producing the A-2, B-1, B-2, D-1 as well as A-1, B-3, C-1, D-2, or E-2 monoclonal antibody. The staining test was performed in accordance with the method described in J. Clin. Microbiol., 28, 1308-1313 (1990).

MDCK cells infected with the human influenza A virus subtype H3N2 strain or B virus strain shown below in a 96-well microplate were washed with PBS (pH 7.4), and then fixed with absolute ethanol at room temperature for 10 minutes, in the same manner as in the case of measuring the neutralization activity in the section 1) of Experimental Example 1. Each hybridoma culture supernatant containing the monoclonal antibody was serially diluted at 4-fold dilutions. These were reacted sequentially with a 500-fold dilution of rabbit anti-human IgG serum (manufactured by Jackson), a 500-fold dilution of goat anti-rabbit IgG serum (manufactured by Cappel), and a 10,000-fold dilution of a peroxidase-rabbit anti-peroxidase complex (manufactured by Cappel) each for 40 minutes, and washed with PBS. Finally, a peroxidase reaction was performed using a PBS solution of 0.01% $H_2O_2$ and 0.3 mg/mL of 3,3'-diaminobenzidine tetrahydrochloride in accordance with the Graham-Karnovsky method in J. Histochem. Cytochem., 14, 291-302 (1966), and the stained cells were observed under an ordinary optical microscope.

A. Influenza a Virus Subtype H3N2 Strains
Ai/68: A/Aichi/2/68 strain (isolated in 1968)
Gz/89: A/Guizhou/54/89 strain (isolated in 1989)
Wy/03: A/Wyoming/3/03 strain (isolated in 2003)
NY/04: A/New York/55/04 strain (isolated in 2004)
Hi/05: A/Hiroshima/52/05 strain (isolated in 2005)
B. Human Influenza B Virus Strains
Vi/87: B/Victoria/2/87 strain (isolated in 1987)
Ma/04: B/Malaysia/2506/04 strain (isolated in 2004)
Mi/93: B/Mie/1/93 strain (isolated in 1993)
Sh/02: B/Shanghai/261/02 strain (isolated in 2002)

The results in Table 2 confirmed that the culture supernatant of the hybridoma producing the A-2 or B-1 monoclonal antibody exhibited a high staining activity for the human influenza A virus subtype H3N2 strains, and it was also confirmed that the culture supernatant of the hybridoma producing the A-1, C-1, or E-2 monoclonal antibody exhibited a high staining activity for the human influenza B virus. These confirmed that these monoclonal antibodies had staining activities for the strains of the influenza A virus subtype H3N2 or the influenza B virus, even for those conserved for about 40 years or for 20 years or more.

Experimental Example 1-4

Neutralization Activity of Hybridoma Culture Supernatants Against Various Influenza Virus Vaccine Strains Neutralization activities against cells infected with the influenza virus vaccine strains in various generations shown in Experimental Example 3 was examined for the supernatant of the hybridoma producing the B-1, D-1 as well as E-2, or B-3 monoclonal antibody. The neutralization activity was measured in accordance with the techniques in Experimental Example 1.

As a result, the culture supernatant of the hybridoma producing the B-1 monoclonal antibody exhibited neutralization activities against the various viral strains after A/Aichi/2/68 strain (isolated in 1968), and the culture supernatant of the hybridoma producing the D-1 monoclonal antibody exhibited neutralization activities against the various viral strains after A/Guizhou/54/89 strain (isolated in 1989) of the various viral strains derived from the human influenza A virus subtype 3H2N. The culture supernatant of the hybridoma producing the E-2 or B-3 monoclonal antibody exhibited neutralization activities against the various influenza B virus strains after B/Victoria/2/87 strain (isolated in 1987). These confirmed that these monoclonal antibodies exhibited neutralization activities against the viral strains from the influenza A virus subtype H3N2 or the influenza B virus, even for those conserved for about 40 years or for 20 years or more (FIG. 2).

Experimental Example 1-5

Base Sequence of Variable Region of Each Human Anti-Human Influenza Virus Antibody From the results of the above-mentioned experiment, it was thought that the B-1, D-1, as well as E-2, or B-3

TABLE 2

Staining activity of hybridoma culture supernatants in cells infected with influenza vaccine strains in various generations

| HnMAb | A H3N2 | | | | | B Victoria-group | | B Yamagata-group | |
| --- | --- | --- | --- | --- | --- | --- | --- | --- | --- |
| | Ai/68 | Gz/89 | Wy/03 | NY/04 | Hi/05 | Vi/87 | Ma/04 | Mi/93 | Sh/02 |
| A-2 | >128 | >128 | >128 | >128 | >128 | | | | |
| B-1 | 128 | >128 | >128 | >128 | >128 | | | | |
| B-2 | <2 | >128 | >128 | 128 | >128 | | | | |
| D-1 | <2 | >128 | >128 | >128 | >128 | | | | |
| A-1 | | | | | | >128 | >128 | >128 | >128 |
| B-3 | | | | | | 32 | 8 | 32 | 32 |
| C-1 | | | | | | 128 | 128 | >128 | >128 |
| D-2 | | | | | | <2 | <2 | <2 | 2 |
| E-2 | | | | | | >128 | 128 | 128 | >128 | monoclonal antibody (human anti-human influenza virus antibody) could recognize a region conserved for 40 years or about 20 years in the human influenza A virus subtype H3N2 or the human influenza B virus. Thus, the base sequences encoding the variable regions of these monoclonal antibodies were examined in this experimental example.

1) Extraction of Total RNA and RT-PCR Specific for Human Antibody (IgG) Sequence The hybridoma obtained by cloning as described above was homogenized in a nucleic acid extraction reagent (RNAiso™, TakaraBio), and total RNA was purified in accordance with the protocol of the kit.

cDNA was synthesized using a part of the total RNA sample after purification and using the following RT primer or dT primer designed specifically for the sequences of the H chain and L chain constant regions of a gene encoding a human antibody (IgG).

Human_IgGH_RT_Primer:
(SEQ ID NO: 13)
TGGAGGGCACGGTCACCACGC

Human_IgGL_RT_Primer:
(SEQ ID NO: 14)
TTGTGACGGGCGAGCTCAGGC

RACE PCR was further performed using the following PCR primers located upstream of the above-mentioned primers.

Human_IgGH_PCR_Primer:
(SEQ ID NO: 15)
AAGGTGTGCACGCCGCTGGTC

Human_IgGL (κ)_PCR_Primer:
(SEQ ID NO: 16)
GTGCTGCTGAGGCTGTAGGTG

Human IgL (λ)PCR Primer 1:
(SEQ ID NO: 17)
CCAYTGTCTTCTCCACRGTRCTCYC

Human IgL (λ) PCR Primer 2:
(SEQ ID NO: 18)
TCAGAGGAGGRYGGGAACAGAGTG

2) Purified PCR Products

The resulting PCR product was electrophoresed on 3% agarose gel, and the PCR product was purified from the resulting band. The base sequence of DNA was analyzed in the purified PCR product. The analysis was carried out by AB13730 Sequencer (ABI) using BigDye® Terminators v3.1 Cycle Sequencing Kit (ABI). As a result, the sequences represented in SEQ ID NOS: 5 to 12 shown below were identified for the heavy chain variable region sequence and light chain variable region sequence of each monoclonal antibody. Further, the heavy chain variable region sequence and the light chain variable region sequence, and translated amino acid sequences therefrom for the each monoclonal antibody were as shown in FIGS. 3 to 10 (SEQ ID NOS: 19 to 26).

A-1. Human Antibody (B-1) Against Human Influenza a Virus Subtype H3N2

Heavy chain variable region sequence:
(SEQ ID NO: 5)
GAGGAGAACCTGTTGCAGTCTGGGGGAGGCTTGGTCCAGCCGGGGGGGTCCCTGAGACTCTC

CTGTGCAGGCTCTGGATTCACGTTTAGTACTTACGCCATGACCTGGGTCCGCCAGGCTCCAG

GACAGGGGCTGGAGTGGGTCTCCTCTATTAGCGGTAGTGGTGAAATTTCCTATTACGCAGAC

TCCGTGAAGGGCCTGTTCACCATCTCCAGGGACAATTCCAAGGACACAGTGTTTCTGCAAAT

GACCAGCCTGAGAGCCGAAGACACGGCCGTATATTACTGTGCGAAATCCGACGTTTGGGAGG

GTTATCGACCCTCAAAAGATGCTCTTCATATGTGGGGCCAAGGGACAATGGTCACCGTCTCT

TCA.

Light chain variable region sequence:
(SEQ ID NO: 6)
GACGTCCAGATGACTCAGTCTCCATCCTCCCTGTCTGCATCTGTGGGAGACAGAGTCACCAT

CACTTGTCGGGCAAGTCAGAGCGTGAGCAATTATGTGAATTGGTATCAACAGAAGCCAGGGA

GAGCCCCTAGGCTCCTCATCTCTAGTGCGTCCAATTTGTGGGCTGGGGTCCCGCCAAGGTTC

AGTGGCCGTGGAGAAGAGACAGACTTCACTCTCACCATCACCAGTCTGCAACCTGAAGATTC

TGCAGTTTACTACTGTCAACAGAGTTACAGTGACCTTCTCAGTTTCGGCGGAGGGACCAAGG

TGGAGATCAAA.

A-2. Human Antibody (D-1) Against Human Influenza a Virus Subtype H3N2

Heavy chain variable region sequence:
(SEQ ID NO: 7)
CAGGTGCAGCTGGTGCAATCTGGGTCTGAGTTGAAGAAGCCTGGGGCCTCAGTGAAGGTTTC

CTGCAAGGCTTCTGGATACACCTTCACCTCTTATTCTATATATTGGGTGCGACAGGCCCCTG

-continued
```
GACAAGGGCTTGAGTGGATGGGATGGATCAACACCAACACTGGGAACCCAAGCTATGCCCAG

GGCTTCACAGGACGGTTTGTCTTCTCCTTCGACACCTCTGTCAGCACGGCATATCTGGAGAT

CAGCAGCCTAAAGGCTGAGGACACTGCCGTGTATTACTGTGCGAGAGAGGGAGATTACGATA

TTTTGACTGGTTATTATTATTACTTTGACTACTGGGGCCAGGGAACCCTGGTCACCGTCTCC

TCA.
```

Light chain variable region sequence:
(SEQ ID NO: 8)
```
CAGACTGTGGTGACCCAGGAGCCATCGTTCTCAGTGTCCCTGGAGGGACAGTCACACTCAC

TTGTGGCTTGAGCTCTGGCTCAGTCTCTCCTAGTTACTACGCCAGCTGGTACCAGCAGACCC

CAGGCCAGGCTCCACGCACGCTCATCTACAACACAAACACTCGCTCCTCTGGGGTCCCTGAT

CGCTTCTCTGGCTCCTTCCTTGGGAGCGACGCTGCCCTCACCATCACGGGGGCCCAGGCAGA

TGATGAGTCTGATTATTTCTGTGTGCTGTATATGCCTAGTGGCGATTGGGTTTTCGGCGGAG

GGACCAAGCTGACCGTCCTAGGT.
```

B-1. Human Antibody (E-2) Against Human Influenza B Virus

Heavy chain variable region sequence:
(SEQ ID NO: 9)
```
CAGGTGCAGTTGCAGGAGTCGGGCCCAGGACTGGTGAAGCCTTTACAGACCCTGTCCCTCAC

CTGCGTTGTCTCTGGTGACTCCATCAGCAGGGGTGGTTACTACTGGAGTTGGGTCCGCCAGC

CCCCAGAGAGGGGCCTGGAGTGGATTGGGGACATCTATCACAGTGGGAGTACCAACTACAAC

CCGGCCCTCAAGAGTCGAACTACCATCTCAGTAGAGACGTCCAAGAACCAGTTCTCCCTGCA

GCTGAACTCTGTGACCGCCGCAGACACGGCCGTGTATTACTGTGCCAGAGAGCCTCCACCTG

ACTACAGTGACTACAAGGTTGGGAAGGGTTATTTTGACTACTGGGGCCAGGGAGCCCTGGTC

ACCGTCTCCTCA.
```

Light chain variable region sequence:
(SEQ ID NO: 10)
```
GAAATTGTGTTGGCACAGTCTCCAGCCACCCTGTCTTTGTCTCCAGGGGAAAGAGCCACCCT

CTCCTGCAGGGCCAGTGAGACCGTTGACACCTACTTAGCCTGGTACCAACAGAAACCTGGCC

AGGCTCCCAGGCTCCTCATAAATGATGCATCCAAGAGGGCCACTGGCATCCCAGCCAGGTTC

AGTGGCAGTGGGTCTGGGACAGACTTCACTCTCACCATCAGCGGCCTAGAGCCTGAAGATTT

TGCAGTTTATTGGTGTCAGCAGCATAGCAACTGGCCCCCCACCTTCGGCCAAGGGTCACGGC

TGGAGATTAAA.
```

B-2. Human Antibody (B-3) Against Human Influenza B Virus

Heavy chain variable region sequence:
(SEQ ID NO: 11)
```
CAGGTGAAGTTGGTGCAGTCTGGCGGAGGCGCAGTCCAGCCTGGGAGGTCCCTGAGACTCTC

CTGTGAGGCGTCTGGATTCGACTTCACTGTGTATGACATCCACTGGGTCCGCCAGGCTCCAG

GCAAGGGGCTTGAGTGGGTGGCATCTATTTGGCATAACGGAGGAAAAGCATATTATGCGGAC

TCCGTGAAGGGCCGATTCACCGTGTCCAGAGACAATCCCCAGAAGACAGTGTATCTGCAAAT

GAGTGGCCTGAGACCCGAGGACACGGCTACATATTACTGTGCGAGAGAGTTTCCTTTCATGG

GCATCTATGACTACGGCATGGACGCCTGGGGCCAAGGGACCACGGTCACCGTCGCCTCA.
```

-continued
Light chain variable region sequence:
(SEQ ID NO: 12)
CAGTCTGTGCTGGCTCAGCCACCCTCAGCGTCTGGGACCCCCGGGCAGAGGGTCATCATCTC

TTGTTCTGGAACCTCCTCCAACATCGGCGGTAATTCTGTCAACTGGTACCAGCACCCCCCAG

GGGCGGCCCCGAGACTCCTCATCTATACTACCGATCAGCGACCCTCAGGGGTCCCTGACCGA

TTCTCTGGCTCCAAGTCTGGCACCTCTGCCTCCCTGGCCATCAGTGGGCTCCAATCTGAGGA

TGAGGCTGATTATTACTGTGAAGTTTGGGATGACAGCCTGACTCGTCCGGTGTTCGGCGGAG

GGACCAAGTTGACCGTCCTACGT.

Experimental Example 1-6

Staining Activity of Hybridoma Culture Supernatants in Cells Infected with Various Influenza Virus Vaccine Strains Staining activities in cells infected with A/Hiroshima/52/05 (H3N2) strain was examined for the supernatant of the hybridoma producing the A-2, B-1, B-2, or D-1 monoclonal antibody as well as C43 antibody and F49 antibody. The staining test was performed by an ordinary indirect fluorescence antibody method. Here, the C43 antibody used as a control is an antibody against the human influenza A virus, particularly a murine monoclonal antibody against a nucleoprotein (NP). Further, the F49 antibody is an antibody against the human influenza A virus subtype H3N2, particularly a murine monoclonal antibody against HA.

MDCK cells infected with the human influenza A virus subtype H3N2, A/Hiroshima/52/05 strain were washed with PBS (pH 7.4) on an 8-well chamber slide and fixed with absolute ethanol at room temperature for 10 minutes, in the same manner as in the case of measuring the neutralization activity in the section 1) of Experimental Example 1. Each undiluted hybridoma culture supernatant containing the monoclonal antibody was sequentially reacted for 60 minutes with a 1000-fold dilution of fluorescein isothiocyanate (FITC)-labeled rabbit anti-human IgG antibody (manufactured by Jackson). The stained cells washed with PBS were observed under a fluorescence microscope.

Figure 11:
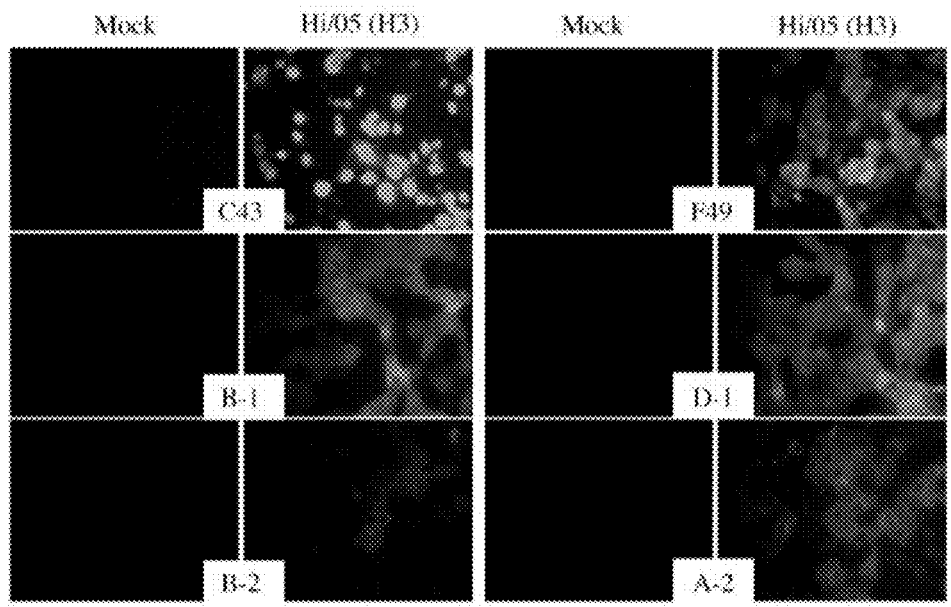
FIG. 11 are images showing the results of confirming cells infected with an influenza virus vaccine strain and stained with a supernatant of each hybridoma producing the A-2, B-1, B-2, or D-1 monoclonal antibody (Experimental Example 1-6).

As a result, the culture supernatant of the hybridoma producing the A-1, B-1, B-2, or D-1 monoclonal antibody exhibited the same staining pattern as that of the murine monoclonal antibody F49 against HA of the human influenza A virus subtype H3N2 (FIG. 11). This led to the speculation that these monoclonal antibodies obtained using the purified HA antigen were antibodies against HA of the influenza A virus subtype H3N2.

Experimental Example 1-7

Staining Activity of Hybridoma Culture Supernatants in Cells Infected with Various Influenza Virus Vaccine Strains Staining activities in cells infected with B/Malaysia/2506/04 strain was examined for the supernatant of the hybridoma producing the B-3 or E-2 monoclonal antibody as well as 9F3 antibody and 9E10 antibody. The staining test was performed by an ordinary indirect fluorescence antibody method. Here, the 9F3 antibody used as a control is an antibody against the human influenza B virus, particularly a murine monoclonal antibody against NP. Further, the 9E10 antibody is an antibody against the human influenza B virus, particularly a murine monoclonal antibody against HA.

MDCK cells infected with the human influenza B virus, B/Malaysia/2506/04 strain were washed with PBS (pH 7.4) on an 8-well chamber slide and fixed with absolute ethanol at room temperature for 10 minutes, in the same manner as in the case of measuring the neutralization activity in the section 1) of Experimental Example 1. Each undiluted hybridoma culture supernatant containing the monoclonal antibody was sequentially reacted for 60 minutes with a 1000-fold dilution of FITC-labeled rabbit anti-human IgG antibody (manufactured by Jackson). The stained cells washed with PBS were observed under a fluorescence microscope.

Figure 12:
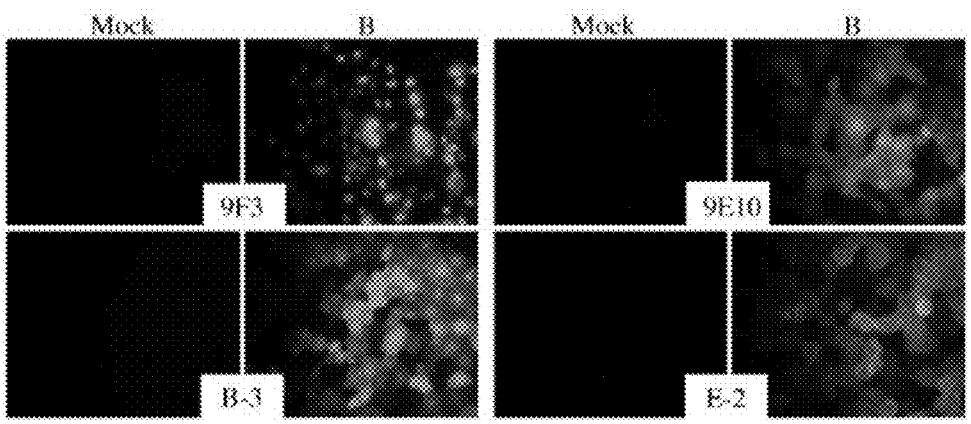
FIG. 12 are images showing the results of confirming cells infected with the influenza virus vaccine strain and stained with a supernatant of each hybridoma producing the B-3 or E-2 monoclonal antibody (Experimental Example 1-7).

As a result, the culture supernatant of the hybridoma producing the B-3 or E-2 monoclonal antibody exhibited the same staining pattern as that of the murine monoclonal antibody 9E10 against HA of the human influenza B virus (FIG. 12). This led to the speculation that these monoclonal antibodies obtained using the purified HA antigen were antibodies against HA of the human influenza B virus.

Experimental Example 1-8

Epitope Mapping

Epitope analysis was performed for the B-1 and D-1 monoclonal antibodies in this example.

A total of 166 sets of peptides were synthesized which were the peptides of 15 residues consecutively selected from 345 amino acid residues which formed the hemagglutinin HA1 region including a signal peptide portion in Hi/05: A/Hiroshima/52/05 strain (isolated in 2005) and which were adjusted so that 13 residues were overlapped. A peptide array in which each peptide from the above-mentioned 166 sets had been immobilized on a glass surface was prepared. The glass surface was blocked with a buffer for blocking (Super Block® TBS manufactured by Piace), and subsequently, each monoclonal antibody diluted to 10 µg/mL with the buffer for blocking was reacted. After incubation, the peptide array was washed three times with TBS containing 0.1% Tween 20, and Cy5-labeled anti-human IgG (H+ L) diluted to 1 µg/mL was reacted. After incubation, the peptide array was washed three times with the above-mentioned tris buffered saline (TBS) and washed thoroughly with a 3 mM citrate buffer (SSC), then dried, and the fluorescence was measured by a fluorescence scanner to detect the peptide capable of reacting with the monoclonal antibody. As a control, an experiment in which no monoclonal antibody was added and other manipulations were performed in the same manner was performed simultaneously. An antigen antibody reaction was performed using the B-1 or D-1 monoclonal antibody, and epitope analysis was performed by an overlap peptide scanning method. Specifically, the analysis was conducted in accordance with the protocol of RepliTope™ Microarrays (JPT Peptide Technologies Gmbh Germany).

As a result, a neutralization activity was detected in the sites shown in FIG. 13. Two peptide chain portions of hemagglutinin HA1 which reacted with the B-1 or D-1 monoclonal antibody were conserved except one residue in an N terminal side in the five H3N2 viral strains. Thus, it was confirmed that the variation was limited in this region. The 227th amino acid counting from the N-terminus of the amino acid sequence which forms hemagglutinin HA1 of the human influenza A virus subtype H3N2 is serine (S) or proline (P), but such difference has no effect on the neutralization activity. The amino acid residue at this position is also S or P in the literature (Karoline et al Virology J., 5, 40 (2008)). The variant amino acid at position 173 is asparagine (N) or lysine (K), that in the virus vaccine strains other than A/Aichi strain in 1968 is K, and that is K or glutamic acid (E) in the literature. Further, the amino acid residues at positions 229 and 230 are different and are arginine (R) or glycine (G) and isoleucine (I) or valine (V), respectively, in the literature (Underwood, Mol. Immunol., 21, 7 (1987)). The amino acid residues at positions 238 and 239 are different and are K or N and P or R, respectively, in the sequences registered in GenBank.

The two peptide chain portions recognized by the B-1 and D-1 monoclonal antibodies are conformationally close, and thus these antibodies are estimated to conformationally recognize the highly conservative two chains and are anticipated to be highly resistant to mutation of the virus (FIG. 14). The epitope portions recognized by the B-1 and D-1 monoclonal antibodies are different from the epitope recognized by the antibody (F10 antibody, J. Sui et al. Nature structural & molecular biology (2009)) which widely neutralizes the publicly known influenza virus strains. Thus, the viral type which can be neutralized by these monoclonal antibodies is thought to be different.

Further, the epitopes were searched by epitope database (http://www.immuneepitope.org/doc//influenza/index.html) linked to NIAID (National Institute of Allergy and Infectious Disease). As a result, although there was a rabbit polyclonal antibody (No. 42, 63) against a wider range of epitopes including the sequences recognized by the B-1 and D-1 monoclonal antibodies concerning linear epitopes, this includes a portion having many mutations. Concerning conformational epitopes, there is a murine monoclonal antibody (No. 34) which recognizes the epitope formed of partially overlapped amino acid residues at positions 229 and 230, but this epitope is different from the epitopes corresponding to the portions recognized by the B-1 and D-1 monoclonal antibodies. Therefore, the epitopes recognized by the B-1 and D-1 monoclonal antibodies are thought to be novel (see FIG. 15).

In FIG. 15: the portions recognized by the B-1 and D-1 monoclonal antibodies are shown in italic type; horizontal lines denote the numbers and the epitope portions described in Table 6 or B cell epitopes in the above-mentioned database; stars denote the epitope portions of No. 34 in Table 9 describing the conformational antibody against influenza in the same database; and triangles denote the sites at which the amino acid had been substituted in the strains registered in the literature or Pub Med other than the above-mentioned 5 strains.

Example 2

Production of Human Anti-Human Influenza Virus Antibody

In this example, the culture of the hybridomas R1D8 and K4E7 cloned in Example 1 is described, and the production of the B-1 monoclonal antibody (hereinafter, referred to as B-1 antibody) and the D-1 monoclonal antibody (hereinafter, referred to as D-1 antibody) is described.

Each hybridoma was cultured on a large scale using a serum-free medium (Hybridoma-SFM™; GIBCO) in an incubator containing 5% $CO_2$ at 37° C. The culture supernatant was collected, an antibody molecule was adsorbed to a Protein G Sepharose™ (Protein G Sepharose™ 4 Fast Flow; GE healthcare) column, which was then washed twice with PBS, and the antibody molecule was eluted with a solution of 0.17 M glycine at pH 2.3. The eluted antibody molecule was dialyzed against PBS using a dialysis membrane (Spectra/Por® (fractioned molecules); 6 K to 8 K; Nippon Genetics), and collected. Final yields of R1D8 and K4E7 were 0.249 mg/L and 24.38 mg/L, respectively.

Experimental Example 2-1

Effects of Human Anti-Human Influenza Virus Antibody (Preventive Effects)

In this experimental example, a survival rate and an effect on body weight changes were identified when the B-1 antibody or the D-1 antibody obtained by purifying in Example 2 was prophylactically administered to mice.

The B-1 antibody or the D-1 antibody obtained by purifying in Example 2 was intraperitoneally administered at a dosage of 100 μg/mouse to 4-week old female Balb/c mice (5 in one group), and $1×10^5$ FFU/mouse of an influenza virus A/Guizhou/54/89xA/PR/8/34 (H3N2) strain was nasally inoculated thereto after 24 hours. As a control group, 0.5 mL/mouse of PBS was administered instead of the monoclonal antibody. The A/Guizhou/54/89xA/PR/8/34 (H3N2) strain is a re-assortant virus obtained by replacing HA and NA in an A/PR/8/34 (H1N1) strain with those in an A/Guizhou/54/89 (H3N2) strain.

Figure 16:
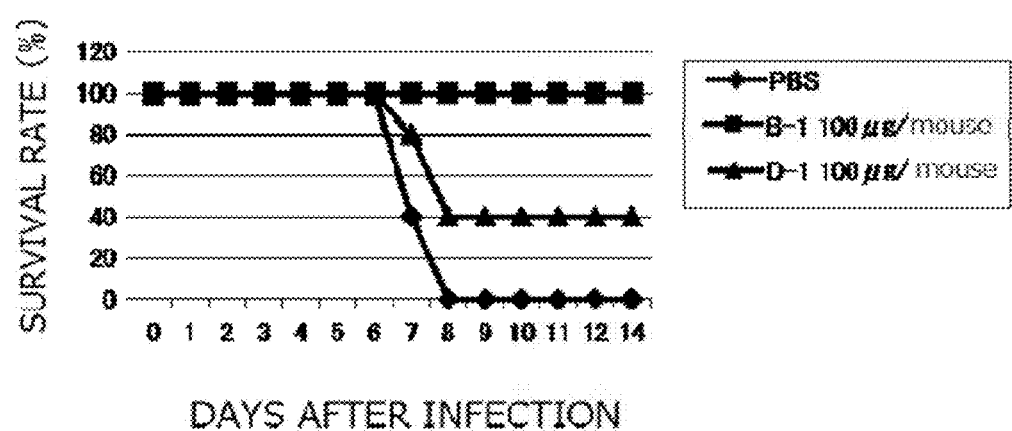
FIG. 16 is a graph showing survival rates when each of the B-1 and D-1 monoclonal antibodies is prophylactically administered to five mice (Experimental Example 2-1).
Figure 17:
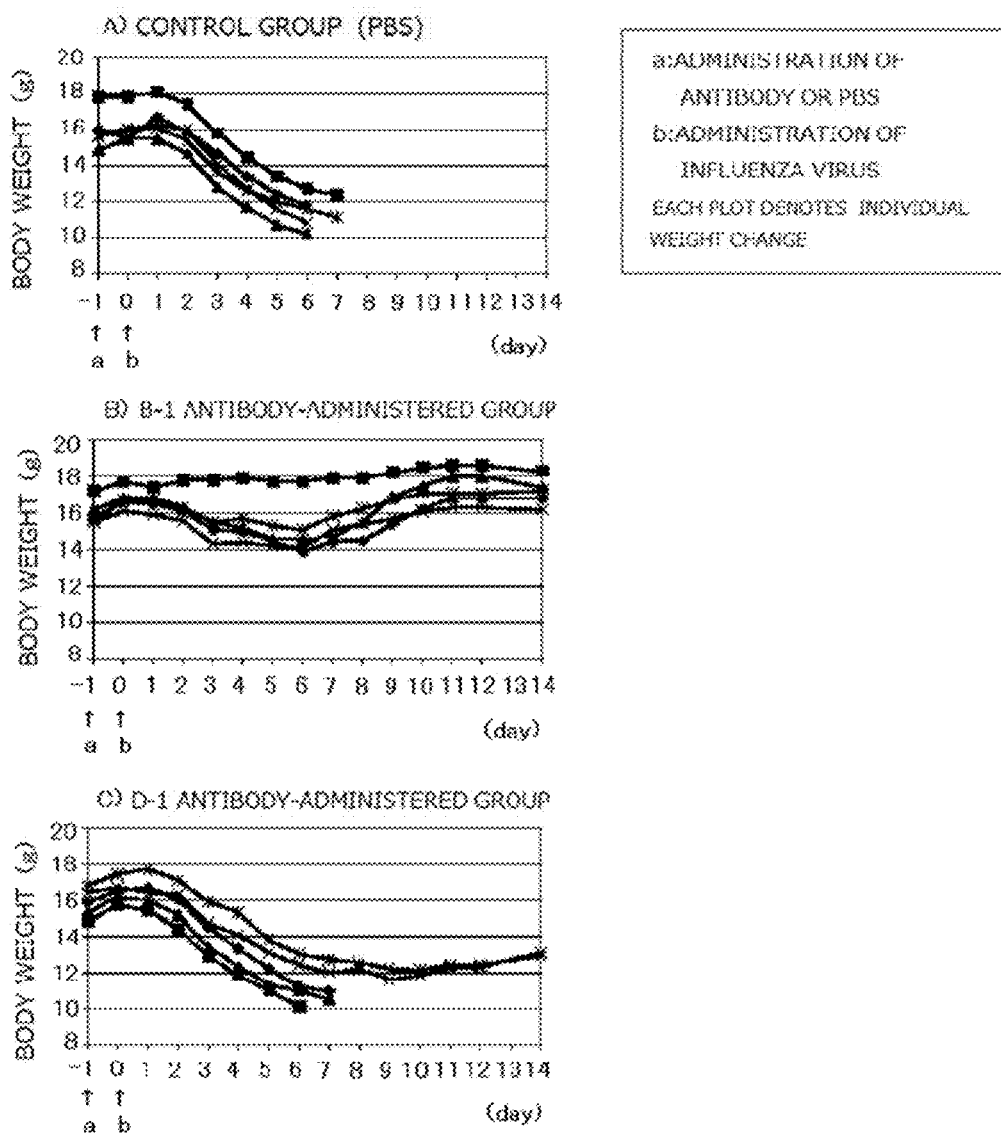
FIG. 17 are graphs showing body weight changes when each of the B-1 and D-1 monoclonal antibodies is prophylactically administered to five mice. Each plot shows the body weight change of each mouse (Experimental Example 2-1).

The survival rates in the D-1 antibody-administered group and B-1 antibody-administered group were 40% and 100%, respectively, whereas the survival rate in the control group was 0%. In particular, a good effect was obtained with the B-1 antibody (FIG. 16). Further, concerning the body weight change after the infection with the virus, the body weight was slightly reduced in the B-1 antibody-administered group. Meanwhile, the body weight in the D-1 antibody-administered group was reduced to a similar degree to that in the control group (FIG. 17). In FIG. 17, the body weight change in an individual mouse is shown in each plot.

Experimental Example 2-2

Effects of Human Anti-Human Influenza Virus Antibody (Therapeutic Effects)

In this experimental example, a survival rate and an effect on body weight changes were identified when the B-1 antibody or the D-1 antibody obtained by purifying in Example 2 was therapeutically administered to mice.

An influenza virus A/Guizhou/54/89xA/PR/8/34 (H3N2) strain at a dosage of $1×10^5$ FFU/mouse was nasally inoculated to 4-week old female Balb/c mice (5 in one group), and the B-1 antibody or the D-1 antibody obtained by purifying in Example 2 was intraperitoneally administered at a dosage of 100 μg/mouse after 24 hours. As a control group, 0.5 mL/mouse of PBS was administered instead of the monoclonal antibody.

Figure 18:
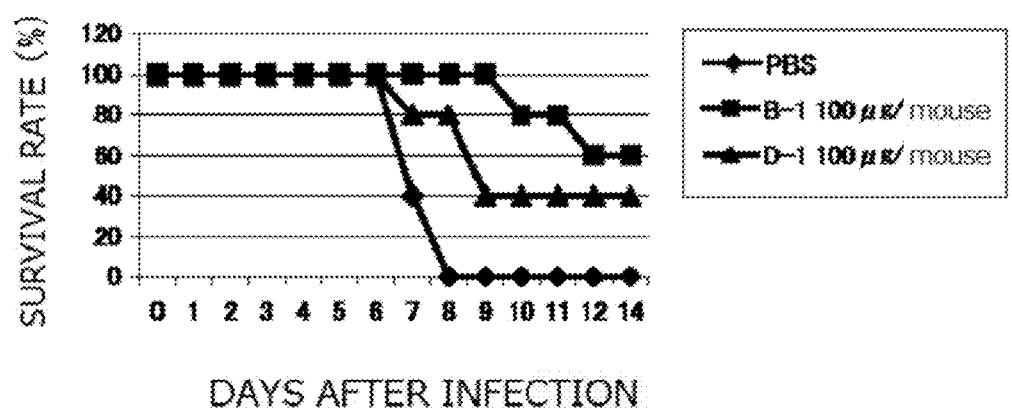
FIG. 18 is a graph showing survival rates when each of the B-1 and D-1 monoclonal antibodies is therapeutically administered to five mice (Example 2-2).

The survival rates in the D-1 antibody-administered group and B-1 antibody-administered group were 40% and 60%, respectively, whereas the survival rate in the control group was 0% (FIG. 18). Further, concerning the body weight change after the infection with the virus, the body weight was reduced rather slightly with the B-1 antibody as compared to the control group. Meanwhile, the body weight was reduced to a similar degree with the D-1 antibody to that in the control group (FIG. 19). In FIG. 19, the body weight change in an individual mouse is shown in each plot.

INDUSTRIAL APPLICABILITY

As described above in detail, in the antibodies of the present invention, the antibody against the human influenza A virus subtype H3N2 has a neutralization activity against at least an A/Hiroshima/52/05 strain (isolated in 2005) viral strain, and the antibody against the human influenza B virus has a neutralization activity against at least a B/Malaysia/2506/04 strain (isolated in 2004) viral strain. Further, the antibodies of the present invention also have neutralization activities against influenza virus vaccine strains in various generations including: various viral strains from the human influenza A virus subtype H3N2, such as an A/Aichi/2/68 strain (isolated in 1968), an A/Guizhou/54/89 strain (isolated in 1989), an A/Wyoming/3/03 strain (isolated in 2003), and an A/New York/55/04 strain (isolated in 2004); and various viral strains from the human influenza B virus, such as a B/Victoria/2/87 strain (isolated in 1987), a B/Mie/1/93 strain (isolated in 1993), and a B/Shanghai/261/02 strain (isolated in 2002).

That is, the antibody against the human influenza A virus subtype H3N2 of the present invention has an activity against a region which has been conserved for about 20 years, and also includes one having an activity against a region which has been conserved for 40 years or more. The antibody against the human influenza B virus also has an activity against a region which has been conserved for 20 years or more. Meanwhile, an HI (hemagglutination inhibition) activity in the antibody of the present invention is equal to or less than the detection limit.

Further, when administered prophylactically or therapeutically in vivo, the antibody against the human influenza A virus subtype H3N2 of the present invention exhibits effects on a survival rate and a weight loss in at least the infection with the influenza virus A/Guizhou/54/89xA/PR/8/34 (H3N2) strain.

Due to the above-mentioned properties, the human anti-human influenza virus antibody of the present invention has effects particularly on regions conserved in an influenza virus to be easily mutated. The influenza A virus subtype H3N2 is a subtype which caused a worldwide epidemic in the past, and strains resistant to medicaments such as amantadine having the anti-influenza virus action have been increasing in recent years. However, the composition including the human anti-human influenza virus antibody of the present invention is expected to have a therapeutic effect on influenza even when new influenza virus occurs and becomes epidemic in the future. The human anti-human influenza virus antibody of the present invention has a neutralization activity against the human influenza A virus subtype H3N2 or the human influenza B virus. Thus, the composition including at least one or more kinds of such antibodies is expected to be utilized as a therapeutic drug and a prophylactic drug for influenza.

SEQUENCE LISTING

```
<160> NUMBER OF SEQ ID NOS: 84

<210> SEQ ID NO 1
<211> LENGTH: 9
<212> TYPE: PRT
<213> ORGANISM: Influenza A virus

<400> SEQUENCE: 1

Asn Phe Asp Lys Leu Tyr Ile Trp Gly
1               5

<210> SEQ ID NO 2
<211> LENGTH: 9
<212> TYPE: PRT
<213> ORGANISM: Influenza A virus

<400> SEQUENCE: 2

Lys Phe Asp Lys Leu Tyr Ile Trp Gly
1               5

<210> SEQ ID NO 3
<211> LENGTH: 13
<212> TYPE: PRT
<213> ORGANISM: Influenza A virus

<400> SEQUENCE: 3

Ser Ser Arg Ile Ser Ile Tyr Trp Thr Ile Val Lys Pro
1               5                   10

<210> SEQ ID NO 4
<211> LENGTH: 13
<212> TYPE: PRT
<213> ORGANISM: Influenza A virus
```

<400> SEQUENCE: 4

Pro Ser Arg Ile Ser Ile Tyr Trp Thr Ile Val Lys Pro
1               5                   10

<210> SEQ ID NO 5
<211> LENGTH: 375
<212> TYPE: DNA
<213> ORGANISM: Homo sapiens

<400> SEQUENCE: 5

| | | | | | |
|---|---|---|---|---|---|
| gaggagaacc | tgttgcagtc | tgggggaggc | ttggtccagc | cggggggtc | cctgagactc | 60 |
| tcctgtgcag | gctctggatt | cacgtttagt | acttacgcca | tgacctgggt | ccgccaggct | 120 |
| ccaggacagg | gctggagtg | ggtctcctct | attagcggta | gtggtgaaat | ttcctattac | 180 |
| gcagactccg | tgaagggcct | gttcaccatc | tccaggaca | attccaagga | cacagtgttt | 240 |
| ctgcaaatga | ccagcctgag | agccgaagac | acggccgtat | attactgtgc | gaaatccgac | 300 |
| gtttgggagg | ttatcgacc | ctcaaaagat | gctcttcata | tgtggggcca | agggacaatg | 360 |
| gtcaccgtct | cttca | | | | | 375 |

<210> SEQ ID NO 6
<211> LENGTH: 320
<212> TYPE: DNA
<213> ORGANISM: Homo sapiens

<400> SEQUENCE: 6

| | | | | | |
|---|---|---|---|---|---|
| gacgtccaga | tgactcagtc | tccatcctcc | ctgtctgcat | ctgtgggaga | cagagtcacc | 60 |
| atcacttgtc | gggcaagtca | gagcgtgagc | aattatgtga | attggtatca | acagaagcca | 120 |
| gggagagccc | ctaggctcct | catctctagt | gcgtccaatt | tgtgggctgg | ggtcccgcca | 180 |
| agttcagtgg | ccgtggagaa | gagacagact | tcactctcac | catcaccagt | ctgcaacctg | 240 |
| aagattctgc | agtttactac | tgtcaacaga | gttacagtga | ccttctcagt | tcggcggag | 300 |
| ggaccaaggt | ggagatcaaa | | | | | 320 |

<210> SEQ ID NO 7
<211> LENGTH: 375
<212> TYPE: DNA
<213> ORGANISM: Homo sapiens

<400> SEQUENCE: 7

| | | | | | |
|---|---|---|---|---|---|
| caggtgcagc | tggtgcaatc | tgggtctgag | ttgaagaagc | ctggggcctc | agtgaaggtt | 60 |
| tcctgcaagg | cttctggata | caccttcacc | tcttattcta | tatattgggt | gcgacaggcc | 120 |
| cctggacaag | ggcttgagtg | gatgggatgg | atcaacacca | cactgggaa | cccaagctat | 180 |
| gcccagggct | tcacaggacg | gtttgtcttc | tccttcgaca | cctctgtcag | cacggcatat | 240 |
| ctggagatca | gcagcctaaa | ggctgaggac | actgccgtgt | attactgtgc | gagagaggga | 300 |
| gattacgata | ttttgactgg | ttattattat | actttgact | actggggcca | gggaaccctg | 360 |
| gtcaccgtct | cctca | | | | | 375 |

<210> SEQ ID NO 8
<211> LENGTH: 333
<212> TYPE: DNA
<213> ORGANISM: Homo sapiens

```
<400> SEQUENCE: 8
cagactgtgg tgacccagga gccatcgttc tcagtgtccc ctggagggac agtcacactc      60
acttgtggct tgagctctgg ctcagtctct cctagttact acgccagctg gtaccagcag     120
accccaggcc aggctccacg cacgctcatc tacaacacaa acactcgctc ctctggggtc     180
cctgatcgct tctctggctc cttccttggg agcgacgctg ccctcaccat cacggggggcc    240 caggcagatg atgagtctga ttatttctgt gtgctgtata tgcctagtgg cgattgggtt     300
ttcggcggag ggaccaagct gaccgtccta ggt                                  333

<210> SEQ ID NO 9
<211> LENGTH: 384
<212> TYPE: DNA
<213> ORGANISM: Homo sapiens

<400> SEQUENCE: 9
caggtgcagt tgcaggagtc gggcccagga ctggtgaagc ctttacagac cctgtccctc      60
acctgcgttg tctctggtga ctccatcagc agggtggtt actactggag ttgggtccgc     120
cagcccccag agaggggcct ggagtggatt gggacatct atcacagtgg gagtaccaac     180
tacaacccgg ccctcaagag tcgaactacc atctcagtag acacgtccaa gaaccagttc     240
tccctgcagc tgaactctgt gaccgccgca gacacggccg tgtattactg tgccagagag     300
cctccacctg actacagtga ctacaaggtt gggaagggtt attttgacta ctggggccag     360
ggagccctgg tcaccgtctc ctca                                            384

<210> SEQ ID NO 10
<211> LENGTH: 321
<212> TYPE: DNA
<213> ORGANISM: Homo sapiens

<400> SEQUENCE: 10
gaaattgtgt tggcacagtc tccagccacc ctgtctttgt ctccagggga aagagccacc      60
ctctcctgca gggccagtga gaccgttgac acctacttag cctggtacca acagaaacct     120
ggccaggctc ccaggctcct cataaatgat gcatccaaga gggccactgg catcccagcc     180
aggttcagtg gcagtgggtc tgggacagac ttcactctca ccatcagcgg cctagagcct     240
gaagattttg cagtttattg gtgtcagcag catagcaact ggcccccac cttcggccaa     300 gggtcacggc tggagattaa a                                               321

<210> SEQ ID NO 11
<211> LENGTH: 369
<212> TYPE: DNA
<213> ORGANISM: Homo sapiens

<400> SEQUENCE: 11
caggtgaagt tggtgcagtc tggcggaggc gcagtccagc ctgggaggtc cctgagactc      60
tcctgtgagg cgtctggatt cgacttcact gtgtatgaca tccactgggt ccgccaggct     120
ccaggcaagg ggcttgagtg ggtggcatct atttggcata acggaggaaa agcatattat     180
gcggactccg tgaagggccg attcaccgtg tccagagaca atcccagaa cacagtgtat     240 ctgcaaatga gtggcctgag acccgaggac acggctacat attactgtgc gagagagttt     300
cctttcatgg gcatctatga ctacggcatg gacgcctggg gccaagggac cacggtcacc     360
gtcgcctca                                                             369
```

<210> SEQ ID NO 12
<211> LENGTH: 333
<212> TYPE: DNA
<213> ORGANISM: Homo sapiens

<400> SEQUENCE: 12

```
cagtctgtgc tggctcagcc accctcagcg tctgggaccc ccgggcagag ggtcatcatc      60
tcttgttctg gaacctcctc aacatcggc ggtaattctg tcaactggta ccagcacccc     120
ccaggggcgg ccccgagact cctcatctat actaccgatc agcgaccctc agggcgtccct    180 gaccgattct ctggctccaa gtctggcacc tctgcctccc tggccatcag tgggctccaa    240
tctgaggatg aggctgatta ttactgtgaa gtttgggatg acagcctgac tcgtccggtg    300
ttcggcggag ggaccaagtt gaccgtccta cgt                                 333
```

<210> SEQ ID NO 13
<211> LENGTH: 21
<212> TYPE: DNA
<213> ORGANISM: Artificial
<220> FEATURE:
<223> OTHER INFORMATION: Synthesized oligonucleotide (Human_IgG
      H_RT_primer)

<400> SEQUENCE: 13

```
tggagggcac ggtcaccacg c                                               21
```

<210> SEQ ID NO 14
<211> LENGTH: 21
<212> TYPE: DNA
<213> ORGANISM: Artificial
<220> FEATURE:
<223> OTHER INFORMATION: Synthesized oligonucleotide (Human_IgG
      L_RT_primer)

<400> SEQUENCE: 14

```
ttgtgacggg cgagctcagg c                                               21
```

<210> SEQ ID NO 15
<211> LENGTH: 21
<212> TYPE: DNA
<213> ORGANISM: Artificial
<220> FEATURE:
<223> OTHER INFORMATION: Synthesized oligonucleotide (Human_IgG
      H_PCR_primer)

<400> SEQUENCE: 15

```
aaggtgtgca cgccgctggt c                                               21
```

<210> SEQ ID NO 16
<211> LENGTH: 21
<212> TYPE: DNA
<213> ORGANISM: Artificial
<220> FEATURE:
<223> OTHER INFORMATION: Synthesized oligonucleotide
      (Human_IgGL(kappa)_PCR_Primer)

<400> SEQUENCE: 16

```
gtgctgctga ggctgtaggt g                                               21
```

<210> SEQ ID NO 17
<211> LENGTH: 25
<212> TYPE: DNA
<213> ORGANISM: Artificial
<220> FEATURE:
<223> OTHER INFORMATION: Synthesized oligonucleotide (Human
      IgL(lambda)PCR Primer 1)

```
<400> SEQUENCE: 17
ccaytgtctt ctccacrgtr ctcyc                                         25

<210> SEQ ID NO 18
<211> LENGTH: 24
<212> TYPE: DNA
<213> ORGANISM: Artificial
<220> FEATURE:
<223> OTHER INFORMATION: Synthesized oligonucleotide (Human
      IgL(lambda)PCR Primer2)

<400> SEQUENCE: 18
tcagaggagg ryggaacag agtg                                           24

<210> SEQ ID NO 19
<211> LENGTH: 700
<212> TYPE: DNA
<213> ORGANISM: Homo sapiens

<400> SEQUENCE: 19
ctaatacgac tcactatagg gcaagcagtg gtataacgca gagtacgcgg ggagctctga    60
gagaggagcc cagccctggg aatttcaggt gttttcattt ggtgatcagg actgaacaga   120
gagaactcac catggagttt gggctgagtt ggcttttct tgtggctatt ttaaaaggtg    180
tccagtgtga ggagaacctg ttgcagtctg ggggaggctt ggtccagccg ggggggtccc   240
tgagactctc ctgtgcaggc tctggattca cgtttagtac ttacgccatg acctgggtcc   300
gccaggctcc aggacagggg ctggagtggg tctcctctat tagcggtagt ggtgaaattt   360
cctattacgc agactccgtg aagggcctgt tcaccatctc cagggacaat tccaaggaca   420
cagtgtttct gcaaatgacc agcctgagag ccgaagacac ggccgtatat tactgtgcga   480
aatccgacgt ttgggagggt tatcgaccct caaaagatgc tcttcatatg tggggccaag   540
ggacaatggt caccgtctct tcagcctcca ccaagggccc atcggtcttc ccccctggcac   600 cctcctccaa gagcacctct gggggcacag cggccctggg ctgcctggtc aaggactact   660
tccccgaacc ggtgacggtg tcgtggaact caggcgccct                         700

<210> SEQ ID NO 20
<211> LENGTH: 628
<212> TYPE: DNA
<213> ORGANISM: Homo sapiens

<400> SEQUENCE: 20
aagcagtggt atcaacgcag agtacgcggg gagtctcagt caggacacag cgtggacatg    60
agggtccccg ctcagctcct ggggctcctg ctactctggc tccgaggtgc cagtggtgac   120
gtccagatga ctcagtctcc atcctccctg tctgcatctg tgggagacag agtcaccatc   180
acttgtcggg caagtcagag cgtgagcaat tatgtgaatt ggtatcaaca gaagccaggg   240
agagccccta ggctcctcat ctctagtgcg tccaatttgt gggctgggt cccgccaagt    300 tcagtggccg tggagaagag acagacttca ctctcaccat caccagtctg caacctgaag   360
attctgcagt ttactactgt caacagagtt acagtgacct tctcagtttc ggcggaggga   420
ccaaggtgga gatcaaacga actgtggctg caccatctgt cttcaccttc ccgccatctg   480
atgagcagtt gaaatctgga actgcctctg ttgtgtgcct gctgaataac ttctatccca   540
gagaggccaa agtacagtgg aaggtggata acgccctcca atcgggtaac tcccaggaga   600
gtgtcacaga gcaggacagc aaggacag                                     628
```

```
<210> SEQ ID NO 21
<211> LENGTH: 697
<212> TYPE: DNA
<213> ORGANISM: Homo sapiens

<400> SEQUENCE: 21
ctaatacgac tcactatagg gcaagcagtg gtatcaacgc agagtacgcg gggacccaac      60
aaccacaccc ctcctaagaa gaagccccta gaccacagct ccacaccatg gactggacct     120
ggaggatcct cttcttggtg gcagcagcaa caggtgccca ctcccaggtg cagctggtgc     180
aatctgggtc tgagttgaag aagcctgggg cctcagtgaa ggtttcctgc aaggcttctg     240
gatacacctt cacctcttat tctatatatt gggtgcgaca ggcccctgga caagggcttg     300
agtggatggg atggatcaac accaacactg gaacccaag ctatgcccag ggcttcacag      360
gacggtttgt cttctccttc gacacctctg tcagcacggc atatctggag atcagcagcc     420
taaaggctga ggacactgcc gtgtattact gtgcgagaga gggagattac gatattttga     480
ctggttatta ttattacttt gactactggg gccagggaac cctggtcacc gtctcctcag     540
cctccaccaa gggcccatcg gtcttccccc tggcaccctc ctccaagagc acctctgggg     600
gcacagcggc cctgggctgc ctggtcaagg actacttccc cgaaccggtg acggtgtcgt     660
ggaactcagg cgccctgacc agcggcgtgc acacctt                              697

<210> SEQ ID NO 22
<211> LENGTH: 808
<212> TYPE: DNA
<213> ORGANISM: Homo sapiens

<400> SEQUENCE: 22
ctaatacgac tcactatagg gcaagcagtg gtatcaagca gagtacgcgg ggaggccctg      60
aggaaaacaa accccagctg ggaagcctga gaacacttag ccttcatgag tgtccccacc     120
atggcctgga tgatgcttct cctcggactc cttgcttatg gatcaggagt ggattctcag     180
actgtggtga cccaggagcc atcgttctca gtgtcccctg gagggacagt cacactcact     240
tgtggcttga gctctggctc agtctctcct agttactacg ccagctggta ccagcagacc     300
ccaggccagg ctcccacgca gctcatctac aacacaaaca ctcgctcctc tggggtccct     360
gatcgcttct ctggctcctt ccttgggagc gacgctgccc tcaccatcac ggggccag      420 gcagatgatg agtctgatta tttctgtgtg ctgtatatgc ctagtggcga ttgggttttc     480
ggcggaggga ccaagctgac cgtcctaggt cagcccaagg ctgccccctc ggtcactctg     540
ttcccgccct cctctgagga gcttcaagcc aacaaggcca cactggtgtg tctcataagt     600
gacttctacc cgggagccgt gacagtggcc cggaaggcag atagcagccc cgtcaaggcg     660
ggagtggaga ccaccacacc ctccaaacaa agcaacaaca gtacgcggc cagcagctac      720 ctgagcctga cgcctgagca gtggaagtcc cacaaaagct acagctgcca ggtcacgcat     780
gaagagagca ctgtggagaa gacaatgg                                        808

<210> SEQ ID NO 23
<211> LENGTH: 688
<212> TYPE: DNA
<213> ORGANISM: Homo sapiens

<400> SEQUENCE: 23
ctaatacgac tcactatagg gcaagcagtg gtacaacgca gagtacgcgg ggagggtcct      60
```

```
gctcacatgg gaaatacttt ctgagagtcc tggacctcct gtgcaagaac atgaaacacc    120
tgtggttctt cctcctgctg gtggcagctc ccagatgggt cctgtcccag gtgcagttgc    180
aggagtcggg cccaggactg gtgaagcctt acagaccct gtccctcacc tgcgttgtct    240
ctggtgactc catcagcagg ggtggttact actggagttg ggtccgccag ccccagaga    300 ggggcctgga gtggattggg gacatctatc acagtgggag taccaactac aacccggccc    360
tcaagagtcg aactaccatc tcagtagaga cgtccaagaa ccagttctcc ctgcagctga    420
actctgtgac cgccgcagac acggccgtgt attactgtgc cagagagcct ccacctgact    480
acagtgacta caaggttggg aagggttatt ttgactactg gggccaggga ccctggtca    540 ccgtctcctc agcctccacc aagggcccat cggtcttccc cctggcaccc tcctccaaga    600
gcacctctgg gggcacagcg gccctgggct gcctggtcaa ggactacttc cccgaaccgg    660
tgacggtgtc gtggaactca ggcgccct                                       688
```

```
<210> SEQ ID NO 24
<211> LENGTH: 658
<212> TYPE: DNA
<213> ORGANISM: Homo sapiens

<400> SEQUENCE: 24
ctaatacgac tcactatagg gcaagcagtg gtatcaacgc agagtacgcg ggggaggaac     60
tgctcagtta ggacccagag ggaaccatgg aagcccagc tcagcttctc ttcctcctgc    120
tactctggct cccagatatc actggagaaa ttgtgttggc acagtctcca gccaccctgt    180
ctttgtctcc aggggaaaga gccaccctct cctgcagggc cagtgagacc gttgacacct    240
acttagcctg gtaccaacag aaacctggcc aggctcccag gctcctcata aatgatgcat    300
ccaagagggc cactggcatc ccagccaggt tcagtgcag tgggtctggg acagacttca    360
ctctcaccat cagcggccta gagcctgaag attttgcagt ttattggtgt cagcagcata    420
gcaactggcc ccccaccttc ggccaagggt cacggctgga gattaaacga actgtggctg    480
caccatctgt cttcatcttc ccgccatctg atgagcagtt gaaatctgga actgcctctg    540
ttgtgtgcct gctgaataac ttctatccca gagaggccaa agtacagtgg aaggtggata    600
acgccctcca atcgggtaac tcccaggaga gtgtcacaga gcaggacagc aaggacag     658
```

```
<210> SEQ ID NO 25
<211> LENGTH: 694
<212> TYPE: DNA
<213> ORGANISM: Homo sapiens

<400> SEQUENCE: 25
aagcagtggt atcaacgcag agtacgcggg gagctctggg agaggagccc agcactagaa     60
gtcggcggtg tttccattcg gtgaacagca ctgaacacag aggactcacc atggagtttg    120
ggctgatctg gattttcctc gttgctcttt taggaggtgc ccagtgtcag gtgaagttgg    180
tgcagtctgg cggaggcgca gtccagcctg ggaggtccct gagactctcc tgtgaggcgt    240
ctggattcga cttcactgtg tatgacatcc actgggtccg ccaggctcca ggcaagggc    300 ttgagtgggt ggcatctatt tggcataacg gaggaaaagc atattatgcg gactccgtga    360
agggccgatt caccgtgtcc agagacaatc cccagaagac agtgtatctg caaatgagtg    420
gcctgagacc cgaggacacg gctacatatt actgtgcgag agagtttcct ttcatgggca    480
tctatgacta cggcatggac gcctggggcc aaggaccac ggtcaccgtc gcctcagcct    540
ccaccaaggg cccatcggtc ttccccctgg caccctcctc caagagcacc tctggggca    600
```
cagcggccct gggctgcctg gtcaaggact acttccccga accggtgacg gtgtcgtgga   660
actcaggcgc cctgaccagc ggcgtgcaca cctt   694

<210> SEQ ID NO 26
<211> LENGTH: 818
<212> TYPE: DNA
<213> ORGANISM: Homo sapiens

<400> SEQUENCE: 26
ctaatacgac tcactatagg gcaagcagtg gtatcaacgc agagtacgcg ggaagcagtg    60
gtatcaacgc agagtacgcg gggagcttca gctgtgggta gaagacagg gactcaggac   120 actctccagc atggccagct tccctctcct cctcaccctc ctcactcact gtgcagggtc   180
ctgggcccag tctgtgctgg ctcagccacc ctcagcgtct ggaccccccg gcagagggt   240 catcatctct tgttctggaa cctcctccaa catcggcggt aattctgtca actggtacca   300
gcacccccca ggggcggccc cgagactcct catctatact accgatcagc gaccctcagg   360
ggtccctgac cgattctctg gctccaagtc tggcacctct gcctccctgg ccatcagtgg   420
gctccaatct gaggatgagg ctgattatta ctgtgaagtt tgggatgaca gcctgactcg   480
tccggtgttc ggcggaggga ccaagttgac cgtcctacgt cagcccaagg ctgcccctc   540 ggtcactctg ttcccgccct cctctgagga gcttcaagcc aacaaggcca cactggtgtg   600
tctcataagt gacttctacc cgggagccgt gacagtggcc tggaaggcag atagcagccc   660
cgtcaaggcg ggagtggaga ccaccacacc ctccaaacaa agcaacaaca gtacgcggc   720 cagcagctac ctgagcctga cgcctgagca gtggaagtcc cacaaaagct acagctgcca   780
ggtcacgcat gaagagagca ctgtggagaa gacaatgg   818

<210> SEQ ID NO 27
<211> LENGTH: 169
<212> TYPE: PRT
<213> ORGANISM: Homo sapiens

<400> SEQUENCE: 27

Glu Glu Asn Leu Leu Gln Ser Gly Gly Gly Leu Val Gln Pro Gly Gly
1               5                   10                  15

Ser Leu Arg Leu Ser Cys Ala Gly Ser Gly Phe Thr Phe Ser Thr Tyr
            20                  25                  30

Ala Met Thr Trp Val Arg Gln Ala Pro Gly Gln Gly Leu Glu Trp Val
        35                  40                  45

Ser Ser Ile Ser Gly Ser Gly Glu Ile Ser Tyr Tyr Ala Asp Ser Val
    50                  55                  60

Gly Leu Phe Thr Ile Ser Arg Asp Asn Ser Lys Asp Thr Val Phe Leu
65                  70                  75                  80

Gln Met Thr Ser Leu Arg Ala Glu Asp Thr Ala Val Tyr Tyr Cys Ala
                85                  90                  95

Lys Ser Asp Val Trp Glu Gly Tyr Arg Pro Ser Lys Asp Ala Leu His
            100                 105                 110

Met Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala
                165

<210> SEQ ID NO 28
<211> LENGTH: 177
<212> TYPE: PRT
<213> ORGANISM: Homo sapiens

<400> SEQUENCE: 28

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Asn Tyr
            20                  25                  30

Val Asn Trp Tyr Gln Gln Lys Pro Gly Arg Ala Pro Arg Leu Leu Ile
        35                  40                  45

Ser Ser Ala Ser Asn Leu Trp Ala Gly Val Pro Pro Arg Phe Ser Gly
    50                  55                  60

Arg Gly Glu Glu Thr Asp Phe Thr Leu Thr Ile Thr Ser Leu Gln Pro
65                  70                  75                  80

Glu Asp Ser Ala Val Tyr Tyr Cys Gln Gln Ser Tyr Ser Asp Leu Leu
                85                  90                  95

Ser Phe Gly Gly Gly Thr Lys Val Glu Ile Lys Arg Thr Val Ala Ala
            100                 105                 110

Pro Ser Val Phe Thr Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser

<210> SEQ ID NO 29
<211> LENGTH: 177
<212> TYPE: PRT
<213> ORGANISM: Homo sapiens

<400> SEQUENCE: 29

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Tyr Trp Val Arg Gln Ala Pro Gly Gln Gly Leu Glu Trp Met
        35                  40                  45

Gly Trp Ile Asn Thr Asn Thr Gly Asn Pro Ser Tyr Ala Gln Gly Phe
    50                  55                  60

Thr Gly Arg Phe Val Phe Ser Phe Asp Thr Ser Val Ser Thr Ala Tyr
65                  70                  75                  80

Leu Glu Ile Ser Ser Leu Lys Ala Glu Asp Thr Ala Val Tyr Tyr Cys
                85                  90                  95

Ala Arg Glu Gly Asp Tyr Asp Ile Leu Thr Gly Tyr Tyr Tyr Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser

```
                130                 135                 140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr

<210> SEQ ID NO 30
<211> LENGTH: 210
<212> TYPE: PRT
<213> ORGANISM: Homo sapiens

<400> SEQUENCE: 30

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Pro Ser
                20                  25                  30

Tyr Tyr Ala Ser Trp Tyr Gln Gln Thr Pro Gly Gln Ala Pro Arg Thr
            35                  40                  45

Leu Ile Tyr Asn Thr Asn Thr Arg Ser Ser Gly Val Pro Asp Arg Phe
        50                  55                  60

Ser Gly Ser Phe Leu Gly Ser Asp Ala Ala Leu Thr Ile Thr Gly Ala
65                  70                  75                  80

Gln Ala Asp Asp Glu Ser Asp Tyr Phe Cys Val Leu Tyr Met Pro Ser
                85                  90                  95

Gly Asp Trp Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Arg Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Lys Ser Tyr Ser Cys Gln Val Thr His Glu Gly Ser Thr Val Glu Lys
            195                 200                 205

Thr Met
    210

<210> SEQ ID NO 31
<211> LENGTH: 173
<212> TYPE: PRT
<213> ORGANISM: Homo sapiens

<400> SEQUENCE: 31

Gln Val Gln Leu Gln Glu Ser Gly Pro Gly Leu Val Lys Pro Leu Gln
1               5                   10                  15

Thr Leu Ser Leu Thr Cys Val Val Ser Gly Asp Ser Ile Ser Arg Gly
                20                  25                  30

Gly Tyr Tyr Trp Ser Trp Val Arg Gln Pro Pro Glu Arg Gly Leu Glu
            35                  40                  45

Trp Ile Gly Asp Ile Tyr His Ser Gly Ser Thr Asn Tyr Asn Pro Ala
        50                  55                  60
```

Leu Lys Ser Arg Thr Thr Ile Ser Val Glu Thr Ser Lys Asn Gln Phe
65                  70                  75                  80

Ser Leu Gln Leu Asn Ser Val Thr Ala Ala Asp Thr Ala Val Tyr Tyr
                85                  90                  95

Cys Ala Arg Glu Pro Pro Pro Asp Tyr Ser Asp Tyr Lys Val Gly Lys
            100                 105                 110

Gly Tyr Phe Asp Tyr Trp Gly Gln Gly Ala Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala
                165                 170

<210> SEQ ID NO 32
<211> LENGTH: 171
<212> TYPE: PRT
<213> ORGANISM: Homo sapiens

<400> SEQUENCE: 32

Glu Ile Val Leu Ala Gln Ser Pro Ala Thr Leu Ser Leu Ser Pro Gly
1               5                   10                  15

Glu Arg Ala Thr Leu Ser Cys Arg Ala Ser Glu Thr Val Asp Thr Tyr
            20                  25                  30

Leu Ala Trp Tyr Gln Gln Lys Pro Gly Gln Ala Pro Arg Leu Leu Ile
        35                  40                  45

Asn Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Val Tyr Trp Cys Gln Gln His Ser Asn Trp Pro Pro
                85                  90                  95

Thr Phe Gly Gln Gly Ser Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser
                165                 170

<210> SEQ ID NO 33
<211> LENGTH: 175
<212> TYPE: PRT
<213> ORGANISM: Homo sapiens

<400> SEQUENCE: 33

Gln Val Lys Leu Val Gln Ser Gly Gly Gly Ala Val Gln Pro Gly Arg
1               5                   10                  15

Ser Leu Arg Leu Ser Cys Glu Ala Ser Gly Phe Asp Phe Thr Val Tyr
            20                  25                  30

Asp Ile His Trp Val Arg Gln Ala Pro Gly Lys Gly Leu Glu Trp Val
        35                  40                  45

-continued

Ala Ser Ile Trp His Asn Gly Gly Lys Ala Tyr Tyr Ala Asp Ser Val
        50                  55                  60

Lys Gly Arg Phe Thr Val Ser Arg Asp Asn Pro Gln Lys Thr Val Tyr
 65                  70                  75                  80

Leu Gln Met Ser Gly Leu Arg Pro Glu Asp Thr Ala Thr Tyr Tyr Cys
                85                  90                  95

Ala Arg Glu Phe Pro Phe Met Gly Ile Tyr Asp Tyr Gly Met Asp Ala
               100                 105                 110

Trp Gly Gln Gly Thr Thr Val Thr Val Ala Ser Ala Ser Thr Lys Gly
               115                 120                 125

Pro Ser Val Phe Pro Leu Ala Pro Ser Ser Lys Ser Thr Ser Gly Gly
               130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr
               165                 170                 175

<210> SEQ ID NO 34
<211> LENGTH: 210
<212> TYPE: PRT
<213> ORGANISM: Homo sapiens

<400> SEQUENCE: 34

Gln Ser Val Leu Ala Gln Pro Pro Ser Ala Ser Gly Thr Pro Gly Gln
 1               5                   10                  15

Arg Val Ile Ile Ser Cys Ser Gly Thr Ser Ser Asn Ile Gly Gly Asn
                20                  25                  30

Ser Val Asn Trp Tyr Gln His Pro Pro Gly Ala Ala Pro Arg Leu Leu
                35                  40                  45

Ile Tyr Thr Thr Asp Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Glu Val Trp Asp Asp Ser Leu
                85                  90                  95

Thr Arg Pro Val Phe Gly Gly Gly Thr Lys Leu Thr Val Leu Arg Gln
               100                 105                 110

Pro Lys Ala Ala Pro Ser Val Thr Leu Phe Pro Pro Ser Ser Glu Glu
               115                 120                 125

Leu Gln Ala Asn Lys Ala Thr Leu Val Cys Leu Ile Ser Asp Phe Tyr
               130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
               165                 170                 175

Ala Ala Ser Ser Tyr Leu Ser Leu Thr Pro Glu Gln Trp Lys Ser His
               180                 185                 190

Lys Ser Tyr Ser Cys Gln Val Thr His Glu Gly Ser Thr Val Glu Lys
               195                 200                 205

Thr Met
    210

<210> SEQ ID NO 35
<211> LENGTH: 5
<212> TYPE: PRT

```
<213> ORGANISM: Homo sapiens

<400> SEQUENCE: 35

Thr Tyr Ala Met Thr
1               5

<210> SEQ ID NO 36
<211> LENGTH: 17
<212> TYPE: PRT
<213> ORGANISM: Homo sapiens

<400> SEQUENCE: 36

Ser Ile Ser Gly Ser Gly Glu Ile Ser Tyr Tyr Ala Asp Ser Val Lys
1               5                   10                  15

Gly

<210> SEQ ID NO 37
<211> LENGTH: 16
<212> TYPE: PRT
<213> ORGANISM: Homo sapiens

<400> SEQUENCE: 37

Ser Asp Val Trp Glu Gly Tyr Arg Pro Ser Lys Asp Ala Leu His Met
1               5                   10                  15

<210> SEQ ID NO 38
<211> LENGTH: 11
<212> TYPE: PRT
<213> ORGANISM: Homo sapiens

<400> SEQUENCE: 38

Arg Ala Ser Gln Ser Val Ser Asn Tyr Val Asn
1               5                   10

<210> SEQ ID NO 39
<211> LENGTH: 7
<212> TYPE: PRT
<213> ORGANISM: Homo sapiens

<400> SEQUENCE: 39

Ser Ala Ser Asn Leu Trp Ala
1               5

<210> SEQ ID NO 40
<211> LENGTH: 9
<212> TYPE: PRT
<213> ORGANISM: Homo sapiens

<400> SEQUENCE: 40

Gln Gln Ser Tyr Ser Asp Leu Leu Ser
1               5

<210> SEQ ID NO 41
<211> LENGTH: 5
<212> TYPE: PRT
<213> ORGANISM: Homo sapiens

<400> SEQUENCE: 41

Ser Tyr Ser Ile Tyr
1               5

<210> SEQ ID NO 42
<211> LENGTH: 16
<212> TYPE: PRT
```

```
<213> ORGANISM: Homo sapiens

<400> SEQUENCE: 42

Ile Asn Thr Asn Thr Gly Asn Pro Ser Tyr Ala Gln Gly Phe Thr Gly
1               5                   10                  15

<210> SEQ ID NO 43
<211> LENGTH: 16
<212> TYPE: PRT
<213> ORGANISM: Homo sapiens

<400> SEQUENCE: 43

Glu Gly Asp Tyr Asp Ile Leu Thr Gly Tyr Tyr Tyr Tyr Phe Asp Tyr
1               5                   10                  15

<210> SEQ ID NO 44
<211> LENGTH: 11
<212> TYPE: PRT
<213> ORGANISM: Homo sapiens

<400> SEQUENCE: 44

Leu Ser Ser Gly Ser Val Ser Pro Ser Tyr Tyr
1               5                   10

<210> SEQ ID NO 45
<211> LENGTH: 7
<212> TYPE: PRT
<213> ORGANISM: Homo sapiens

<400> SEQUENCE: 45

Ile Tyr Asn Thr Asn Thr Arg
1               5

<210> SEQ ID NO 46
<211> LENGTH: 9
<212> TYPE: PRT
<213> ORGANISM: Homo sapiens

<400> SEQUENCE: 46

Phe Cys Val Leu Tyr Met Pro Ser Gly
1               5

<210> SEQ ID NO 47
<211> LENGTH: 5
<212> TYPE: PRT
<213> ORGANISM: Homo sapiens

<400> SEQUENCE: 47

Arg Gly Gly Tyr Tyr
1               5

<210> SEQ ID NO 48
<211> LENGTH: 11
<212> TYPE: PRT
<213> ORGANISM: Homo sapiens

<400> SEQUENCE: 48

Asp Ile Tyr His Ser Gly Ser Thr Asn Tyr Asn
1               5                   10

<210> SEQ ID NO 49
<211> LENGTH: 18
<212> TYPE: PRT
<213> ORGANISM: Homo sapiens
```

-continued

```
<400> SEQUENCE: 49

Glu Pro Pro Pro Asp Tyr Ser Asp Tyr Lys Val Gly Lys Gly Tyr Phe
1               5                   10                  15

Asp Tyr

<210> SEQ ID NO 50
<211> LENGTH: 11
<212> TYPE: PRT
<213> ORGANISM: Homo sapiens

<400> SEQUENCE: 50

Arg Ala Ser Glu Thr Val Asp Thr Tyr Leu Ala
1               5                   10

<210> SEQ ID NO 51
<211> LENGTH: 7
<212> TYPE: PRT
<213> ORGANISM: Homo sapiens

<400> SEQUENCE: 51

Asp Ala Ser Lys Arg Ala Thr
1               5

<210> SEQ ID NO 52
<211> LENGTH: 9
<212> TYPE: PRT
<213> ORGANISM: Homo sapiens

<400> SEQUENCE: 52

Gln Gln His Ser Asn Trp Pro Pro Thr
1               5

<210> SEQ ID NO 53
<211> LENGTH: 5
<212> TYPE: PRT
<213> ORGANISM: Homo sapiens

<400> SEQUENCE: 53

Val Tyr Asp Ile His
1               5

<210> SEQ ID NO 54
<211> LENGTH: 17
<212> TYPE: PRT
<213> ORGANISM: Homo sapiens

<400> SEQUENCE: 54

Ser Ile Trp His Asn Gly Gly Lys Ala Tyr Tyr Ala Asp Ser Val Lys
1               5                   10                  15

Gly

<210> SEQ ID NO 55
<211> LENGTH: 14
<212> TYPE: PRT
<213> ORGANISM: Homo sapiens

<400> SEQUENCE: 55

Glu Phe Pro Phe Met Gly Ile Tyr Asp Tyr Gly Met Asp Ala
1               5                   10

<210> SEQ ID NO 56
<211> LENGTH: 11
<212> TYPE: PRT
```

-continued

<213> ORGANISM: Homo sapiens

<400> SEQUENCE: 56

Gly Thr Ser Ser Asn Ile Gly Gly Asn Ser Val
1               5                   10

<210> SEQ ID NO 57
<211> LENGTH: 7
<212> TYPE: PRT
<213> ORGANISM: Homo sapiens

<400> SEQUENCE: 57

Tyr Thr Thr Asp Gln Arg Pro
1               5

<210> SEQ ID NO 58
<211> LENGTH: 9
<212> TYPE: PRT
<213> ORGANISM: Homo sapiens

<400> SEQUENCE: 58

Cys Glu Val Trp Asp Asp Ser Leu Thr
1               5

<210> SEQ ID NO 59
<211> LENGTH: 21
<212> TYPE: PRT
<213> ORGANISM: Influenza A virus

<400> SEQUENCE: 59

Thr Met Pro Asn Asn Asp Asn Phe Asp Lys Leu Tyr Ile Trp Gly Val
1               5                   10                  15

His His Pro Ser Thr
            20

<210> SEQ ID NO 60
<211> LENGTH: 21
<212> TYPE: PRT
<213> ORGANISM: Influenza A virus

<400> SEQUENCE: 60

Thr Met Pro Asn Asn Gly Lys Phe Asp Lys Leu Tyr Ile Trp Gly Val
1               5                   10                  15

His His Pro Ile Thr
            20

<210> SEQ ID NO 61
<211> LENGTH: 21
<212> TYPE: PRT
<213> ORGANISM: Influenza A virus

<400> SEQUENCE: 61

Thr Met Pro Asn Asn Glu Lys Phe Asp Lys Leu Tyr Ile Trp Gly Val
1               5                   10                  15

His His Pro Val Thr
            20

<210> SEQ ID NO 62
<211> LENGTH: 21
<212> TYPE: PRT
<213> ORGANISM: Influenza A virus

<400> SEQUENCE: 62

```
Thr Met Pro Asn Asn Glu Lys Phe Asp Lys Leu Tyr Ile Trp Gly Val
 1               5                  10                  15

His His Pro Gly Thr
            20

<210> SEQ ID NO 63
<211> LENGTH: 17
<212> TYPE: PRT
<213> ORGANISM: Influenza A virus

<400> SEQUENCE: 63

Gly Leu Ser Ser Arg Ile Ser Ile Tyr Trp Thr Ile Val Lys Pro Gly
 1               5                  10                  15

Asp

<210> SEQ ID NO 64
<211> LENGTH: 17
<212> TYPE: PRT
<213> ORGANISM: Influenza A virus

<400> SEQUENCE: 64

Asp Ile Ser Ser Arg Ile Ser Ile Tyr Trp Thr Ile Val Lys Pro Gly
 1               5                  10                  15

Asp

<210> SEQ ID NO 65
<211> LENGTH: 17
<212> TYPE: PRT
<213> ORGANISM: Influenza A virus

<400> SEQUENCE: 65

Asp Ile Pro Ser Arg Ile Ser Ile Tyr Trp Thr Ile Val Lys Pro Gly
 1               5                  10                  15

Asp

<210> SEQ ID NO 66
<211> LENGTH: 17
<212> TYPE: PRT
<213> ORGANISM: Influenza A virus

<400> SEQUENCE: 66

Asn Ile Pro Ser Arg Ile Ser Ile Tyr Trp Thr Ile Val Lys Pro Gly
 1               5                  10                  15

Asp

<210> SEQ ID NO 67
<211> LENGTH: 60
<212> TYPE: PRT
<213> ORGANISM: Influenza A virus

<400> SEQUENCE: 67

Ile Thr Glu Gly Phe Thr Trp Thr Gly Val Thr Gln Asn Gly Gly Ser
 1               5                  10                  15

Asn Ala Cys Lys Arg Gly Pro Gly Ser Gly Phe Phe Ser Arg Leu Asn
                20                  25                  30

Trp Leu Thr Lys Ser Gly Ser Thr Tyr Pro Val Leu Asn Val Thr Met
                35                  40                  45

Pro Asn Asn Asp Asn Phe Asp Lys Leu Tyr Ile Trp
                50                  55                  60
```

-continued

```
<210> SEQ ID NO 68
<211> LENGTH: 60
<212> TYPE: PRT
<213> ORGANISM: Influenza A virus

<400> SEQUENCE: 68

Ile Asn Glu Asp Phe Asn Trp Thr Gly Val Ala Gln Ser Gly Gly Ser
1               5                   10                  15

Tyr Ala Cys Lys Arg Gly Ser Ile Asn Ser Phe Phe Ser Arg Leu Asn
                20                  25                  30

Trp Leu His Glu Ser Glu His Lys Tyr Pro Ala Leu Asn Val Thr Met
            35                  40                  45

Pro Asn Asn Gly Lys Phe Asp Lys Leu Tyr Ile Trp
    50                  55                  60

<210> SEQ ID NO 69
<211> LENGTH: 60
<212> TYPE: PRT
<213> ORGANISM: Influenza A virus

<400> SEQUENCE: 69

Asn Asn Glu Ser Phe Asn Trp Thr Gly Val Thr Gln Asn Gly Thr Ser
1               5                   10                  15

Ser Ala Cys Lys Arg Arg Ser Asn Asn Ser Phe Phe Ser Arg Leu Asn
                20                  25                  30

Trp Leu Thr Arg Leu Lys Phe Lys Tyr Pro Ala Leu Asn Val Thr Met
            35                  40                  45

Pro Asn Asn Glu Lys Phe Asp Lys Leu Tyr Ile Trp
    50                  55                  60

<210> SEQ ID NO 70
<211> LENGTH: 60
<212> TYPE: PRT
<213> ORGANISM: Influenza A virus

<400> SEQUENCE: 70

Asn Asn Glu Ser Phe Asn Trp Thr Gly Val Thr Gln Asn Gly Thr Ser
1               5                   10                  15

Ser Ser Cys Lys Arg Arg Ser Asn Asn Ser Phe Phe Ser Arg Leu Asn
                20                  25                  30

Trp Leu Thr His Leu Lys Phe Lys Tyr Pro Ala Leu Asn Val Thr Met
            35                  40                  45

Pro Asn Asn Glu Lys Phe Asp Lys Leu Tyr Ile Trp
    50                  55                  60

<210> SEQ ID NO 71
<211> LENGTH: 60
<212> TYPE: PRT
<213> ORGANISM: Influenza A virus

<400> SEQUENCE: 71

Asn Asn Glu Ser Phe Asn Trp Ala Gly Val Thr Gln Asn Gly Thr Ser
1               5                   10                  15

Ser Ala Cys Lys Arg Arg Ser Asn Lys Ser Phe Phe Ser Arg Leu Asn
                20                  25                  30

Trp Leu Thr His Leu Lys Tyr Lys Tyr Pro Ala Leu Asn Val Thr Met
            35                  40                  45

Pro Asn Asn Glu Lys Phe Asp Lys Leu Tyr Ile Trp
    50                  55                  60
```

```
<210> SEQ ID NO 72
<211> LENGTH: 60
<212> TYPE: PRT
<213> ORGANISM: Influenza A virus

<400> SEQUENCE: 72

Gly Val His His Pro Ser Thr Asn Gln Glu Gln Thr Ser Leu Tyr Val
1               5                   10                  15

Gln Ala Ser Gly Arg Val Thr Val Ser Thr Arg Arg Ser Gln Gln Thr
            20                  25                  30

Ile Ile Pro Asn Ile Glu Ser Arg Pro Trp Val Arg Gly Leu Ser Ser
        35                  40                  45

Arg Ile Ser Ile Tyr Trp Thr Ile Val Lys Pro Gly
    50                  55                  60

<210> SEQ ID NO 73
<211> LENGTH: 60
<212> TYPE: PRT
<213> ORGANISM: Influenza A virus

<400> SEQUENCE: 73

G

<210> SEQ ID NO 76
<211> LENGTH: 60
<212> TYPE: PRT
<213> ORGANISM: Influenza A virus

<400> SEQUENCE: 76

Gly Val His His Pro Val Thr Asp Ser Asp Gln Ile Ser Leu Tyr Ala
1               5                   10                  15

Gln Ala Ser Gly Arg Ile Thr Val Ser Thr Lys Arg Ser Gln Gln Thr
            20                  25                  30

Val Ile Pro Asn Ile Gly Tyr Arg Pro Arg Val Arg Asp Ile Ser Ser
        35                  40                  45

Arg Ile Ser Ile Tyr Trp Thr Ile Val Lys Pro Gly
    50                  55                  60

<210> SEQ ID NO 77
<211> LENGTH: 189
<212> TYPE: PRT
<213> ORGANISM: Homo sapiens

<400> SEQUENCE: 77

Met Glu Phe Gly Leu Ser Trp Leu Phe Leu Val Ala Ile Leu Lys Gly
1               5                   10                  15

Val Gln Cys Glu Glu Asn Leu Leu Gln Ser Gly Gly Gly Leu Val Gln
            20                  25                  30

Pro Gly Gly Ser Leu Arg Leu Ser Cys Ala Gly Ser Gly Phe Thr Phe
        35                  40                  45

Ser Thr Tyr Ala Met Thr Trp Val Arg Gln Ala Pro Gly Gln Gly Leu
    50                  55                  60

Glu Trp Val Ser Ser Ile Ser Gly Ser Gly Glu Ile Ser Tyr Tyr Ala
65                  70                  75                  80

Asp Ser Val Lys Gly Leu Phe Thr Ile Ser Arg Asp Asn Ser Lys Asp
                85                  90                  95

Thr Val Phe Leu Gln Met Thr Ser Leu Arg Ala Glu Asp Thr Ala Val
            100                 105                 110

Tyr Tyr Cys Ala Lys Ser Asp Val Trp Glu Gly Tyr Arg Pro Ser Lys
        115                 120                 125

Asp Ala Leu His Met Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala
            180                 185

<210> SEQ ID NO 78
<211> LENGTH: 190
<212> TYPE: PRT
<213> ORGANISM: Homo sapiens

<400> SEQUENCE: 78

Met Arg Val Pro Ala Gln Leu Leu Gly Leu Leu Leu Leu Trp Leu Arg
1               5                   10                  15

Gly Ala Ser Gly Asp Val Gln Met Thr Gln Ser Pro Ser Ser Leu Ser
            20                  25                  30

```
Ala Ser Val Gly Asp Arg Val Thr Ile Thr Cys Arg Ala Ser Gln Ser
         35                  40                  45

Val Ser Asn Tyr Val Asn Trp Tyr Gln Gln Lys Pro Gly Arg Ala Pro
 50                  55                  60

Arg Leu Leu Ile Ser Ala Ser Asn Leu Trp Ala Gly Val Pro Pro
 65                  70                  75                  80

Arg Phe Ser Gly Arg Gly Glu Glu Thr Asp Phe Thr Leu Thr Ile Thr
                 85                  90                  95

Ser Leu Gln Pro Glu Asp Ser Ala Val Tyr Tyr Cys Gln Gln Ser Tyr
                100                 105                 110

Ser Asp Leu Leu Ser Phe Gly Gly Gly Thr Lys Val Glu Ile Lys Arg
                115                 120                 125

Thr Val Ala Ala Pro Ser Val Phe Thr Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp
                180                 185                 190

<210> SEQ ID NO 79
<211> LENGTH: 196
<212> TYPE: PRT
<213> ORGANISM: Homo sapiens

<400> SEQUENCE: 79

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ser Glu Leu Lys Lys
                 20                  25                  30

Pro Gly Ala Ser Val Lys Val Ser Cys Lys Ala Ser Gly Tyr Thr Phe
             35                  40                  45

Thr Ser Tyr Ser Ile Tyr Trp Val Arg Gln Ala Pro Gly Gln Gly Leu
 50                  55                  60

Glu Trp Met Gly Trp Ile Asn Thr Asn Thr Gly Asn Pro Ser Tyr Ala
 65                  70                  75                  80

Gln Gly Phe Thr Gly Arg Phe Val Phe Ser Phe Asp Thr Ser Val Ser
                 85                  90                  95

Thr Ala Tyr Leu Glu Ile Ser Ser Leu Lys Ala Glu Asp Thr Ala Val
                100                 105                 110

Tyr Tyr Cys Ala Arg Glu Gly Asp Tyr Asp Ile Leu Thr Gly Tyr Tyr
            115                 120                 125

Tyr Tyr Phe Asp Tyr Trp Gly Gln Gly Thr Leu Val Thr Val Ser Ser
            130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr
        195

<210> SEQ ID NO 80
```

<211> LENGTH: 269
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: unknown

<400> SEQUENCE: 80

Leu Ile Arg Leu Thr Ile Gly Gln Ala Val Ser Ser Arg Val Arg
1               5                   10                  15

Gly Glu Ala Leu Arg Lys Thr Asn Pro Ser Trp Glu Ala Xaa Glu His
            20                  25                  30

Leu Ala Phe Met Ser Val Pro Thr Met Ala Trp Met Met Leu Leu Leu
            35                  40                  45

Gly Leu Leu Ala Tyr Gly Ser Gly Val Asp Ser Gln Thr Val Val Thr
    50                  55                  60

Gln Glu Pro Ser Phe Ser Val Ser Pro Gly Gly Thr Val Thr Leu Thr
65                  70                  75                  80

Cys Gly Leu Ser Ser Gly Ser Val Ser Pro Ser Tyr Tyr Ala Ser Trp
                85                  90                  95

Tyr Gln Gln Thr Pro Gly Gln Ala Pro Arg Thr Leu Ile Tyr Asn Thr
            100                 105                 110

Asn Thr Arg Ser Ser Gly Val Pro Asp Arg Phe Ser Gly Ser Phe Leu
        115                 120                 125

Gly Ser Asp Ala Ala Leu Thr Ile Thr Gly Ala Gln Ala Asp Asp Glu
    130                 135                 140

Ser Asp Tyr Phe Cys Val Leu Tyr Met Pro Ser Gly Asp Trp Val Phe
145                 150                 155                 160

Gly Gly Gly Thr Lys Leu Thr Val Leu Gly Gln Pro Lys Ala Ala Pro
                165                 170                 175

Ser Val Thr Leu Phe Pro Pro Ser Ser Glu Glu Leu Gln Ala Asn Lys
            180                 185                 190

Ala Thr Leu Val Cys Leu Ile Ser Asp Phe Tyr Pro Gly Ala Val Thr
        195                 200                 205

Val Ala Arg Lys Ala Asp Ser Ser Pro Val Lys Ala Gly Val Glu Thr
    210                 215                 220

Thr Thr Pro Ser Lys Gln Ser Asn Asn Lys Tyr Ala Ala Ser Ser Tyr
225                 230                 235                 240

Leu Ser Leu Thr Pro Glu Gln Trp Lys Ser His Lys Ser Tyr Ser Cys
                245                 250                 255

Gln Val Thr His Glu Gly Ser Thr Val Glu Lys Thr Met
            260                 265

<210> SEQ ID NO 81
<211> LENGTH: 192
<212> TYPE: PRT
<213> ORGANISM: Homo sapiens

<400> SEQUENCE: 81

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Leu Gln Thr Leu Ser Leu Thr Cys Val Val Ser Gly Asp Ser Ile
        35                  40                  45

Ser Arg Gly Gly Tyr Tyr Trp Ser Trp Val Arg Gln Pro Pro Glu Arg

```
            50                  55                  60
Gly Leu Glu Trp Ile Gly Asp Ile Tyr His Ser Gly Ser Thr Asn Tyr
 65                  70                  75                  80

Asn Pro Ala Leu Lys Ser Arg Thr Thr Ile Ser Val Glu Thr Ser Lys
                 85                  90                  95

Asn Gln Phe Ser Leu Gln Leu Asn Ser Val Thr Ala Ala Asp Thr Ala
            100                 105                 110

Val Tyr Tyr Cys Ala Arg Glu Pro Pro Asp Tyr Ser Asp Tyr Lys
        115                 120                 125

Val Gly Lys Gly Tyr Phe Asp Tyr Trp Gly Gln Gly Ala Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

<210> SEQ ID NO 82
<211> LENGTH: 191
<212> TYPE: PRT
<213> ORGANISM: Homo sapiens

<400> SEQUENCE: 82

Met Glu Ala Pro Ala Gln Leu Leu Phe Leu Leu Leu Leu Trp Leu Pro
  1               5                  10                  15

Asp Ile Thr Gly Glu Ile Val Leu Ala Gln Ser Pro Ala Thr Leu Ser
                 20                  25                  30

Leu Ser Pro Gly Glu Arg Ala Thr Leu Ser Cys Arg Ala Ser Glu Thr
             35                  40                  45

Val Asp Thr Tyr Leu Ala Trp Tyr Gln Gln Lys Pro Gly Gln Ala Pro
 50                  55                  60

Arg Leu Leu Ile Asn Asp Ala Ser Lys Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Gly Leu Glu Pro Glu Asp Phe Ala Val Tyr Trp Cys Gln Gln His Ser
            100                 105                 110

Asn Trp Pro Pro Thr Phe Gly Gln Gly Ser Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser
            180                 185                 190

<210> SEQ ID NO 83
<211> LENGTH: 230
<212> TYPE: PRT
<213> ORGANISM: Homo sapiens

<400> SEQUENCE: 83

Ala Val Val Ser Thr Gln Ser Thr Arg Gly Ala Leu Gly Glu Glu Pro
```

```
                1               5                  10                  15
              Ser Thr Arg Ser Arg Cys Phe His Ser Val Asn Ser Thr Glu His
                              20                  25                  30
              Arg Gly Leu Thr Met Glu Phe Gly Leu Ile Trp Ile Phe Leu Val Ala
                              35                  40                  45
              Leu Leu Gly Gly Ala Gln Cys Gln Val Lys Leu Val Gln Ser Gly Gly
                              50                  55                  60
              Gly Ala Val Gln Pro Gly Arg Ser Leu Arg Leu Ser Cys Glu Ala Ser
              65                  70                  75                  80
              Gly Phe Asp Phe Thr Val Tyr Asp Ile His Trp Val Arg Gln Ala Pro
                                  85                  90                  95
              Gly Lys Gly Leu Glu Trp Val Ala Ser Ile Trp His Asn Gly Gly Lys
                              100                 105                 110
              Ala Tyr Tyr Ala Asp Ser Val Lys Gly Arg Phe Thr Val Ser Arg Asp
                              115                 120                 125
              Asn Pro Gln Lys Thr Val Tyr Leu Gln Met Ser Gly Leu Arg Pro Glu
                              130                 135                 140
              Asp Thr Ala Thr Tyr Tyr Cys Ala Arg Glu Phe Pro Phe Met Gly Ile
              145                 150                 155                 160
              Tyr Asp Tyr Gly Met Asp Ala Trp Gly Gln Gly Thr Thr Val Thr Val
                                  165                 170                 175
              Ala Ser Ala Ser Thr Lys Gly Pro Ser Val Phe Pro Leu Ala Pro Ser
                              180                 185                 190
              Ser Lys Ser Thr Ser Gly Gly Thr Ala Ala Leu Gly Cys Leu Val Lys
                              195                 200                 205
              Asp Tyr Phe Pro Glu Pro Val Thr Val Ser Trp Asn Ser Gly Ala Leu
                              210                 215                 220
              Thr Ser Gly Val His Thr
              225                 230

<210> SEQ ID NO 84
<211> LENGTH: 271
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: unknown

<400> SEQUENCE: 84

Tyr Asp Ser Leu Xaa Gly Lys Gln Trp Tyr Gln Arg Arg Val Arg Gly
              1               5                  10                  15
              Lys Gln Trp Tyr Gln Arg Arg Val Arg Gly Glu Leu Gln Leu Trp Val
                              20                  25                  30
              Glu Lys Thr Gly Leu Arg Thr Leu Ser Ser Met Ala Ser Phe Pro Leu
                              35                  40                  45
              Leu Leu Thr Leu Leu Thr His Cys Ala Gly Ser Trp Ala Gln Ser Val
                              50                  55                  60
              Leu Ala Gln Pro Pro Ser Ala Ser Gly Thr Pro Gly Gln Arg Val Ile
              65                  70                  75                  80
              Ile Ser Cys Ser Gly Thr Ser Ser Asn Ile Gly Asn Ser Val Asn
                                  85                  90                  95
              Trp Tyr Gln His Pro Pro Gly Ala Ala Pro Arg Leu Leu Ile Tyr Thr
                              100                 105                 110
              Thr Asp Gln Arg Pro Ser Gly Val Pro Asp Arg Phe Ser Gly Ser Lys
                              115                 120                 125
```

-continued

```
Ser Gly Thr Ser Ala Ser Leu Ala Ile Ser Gly Leu Gln Ser Glu Asp
    130                 135                 140
Glu Ala Asp Tyr Tyr Cys Glu Val Trp Asp Asp Ser Leu Thr Arg Pro
145                 150                 155                 160
Val Phe Gly Gly Gly Thr Lys Leu Thr Val Leu Arg Gln Pro Lys Ala
                165                 170                 175
Ala Pro Ser Val Thr Leu Phe Pro Pro Ser Ser Glu Glu Leu Gln Ala
            180                 185                 190
Asn Lys Ala Thr Leu Val Cys Leu Ile Ser Asp Phe Tyr Pro Gly Ala
        195                 200                 205
Val Thr Val Ala Trp Lys Ala Asp Ser Ser Pro Val Lys Ala Gly Val
    210                 215                 220
Glu Thr Thr Thr Pro Ser Lys Gln Ser Asn Asn Lys Tyr Ala Ala Ser
225                 230                 235                 240
Ser Tyr Leu Ser Leu Thr Pro Glu Gln Trp Lys Ser His Lys Ser Tyr
                245                 250                 255
Ser Cys Gln Val Thr His Glu Glu Ser Thr Val Glu Lys Thr Met
                260                 265                 270
```

The invention claimed is:

1. An isolated human anti-human influenza virus monoclonal antibody, comprising a variable region comprising:
 a heavy chain comprising the amino acid sequence of SEQ ID NO: 31 and a light chain comprising the amino acid sequence of SEQ ID NO: 32; or
 a heavy chain comprising the amino acid sequence of SEQ ID NO: 33 and a light chain comprising the amino acid sequence of SEQ ID NO: 34.

2. The isolated human anti-human influenza virus monoclonal antibody according to claim 1, comprising a neutralization activity against a human influenza B virus.

3. The isolated human anti-human influenza virus monoclonal antibody according to claim 1, comprising a neutralization activity against at least a B/Malaysia/2506/04 strain.

4. The isolated human anti-human influenza virus monoclonal antibody according to claim 1, wherein an antigen of the isolated anti-human influenza virus monoclonal antibody is a human influenza virus B/Malaysia/2506/04 strain.

5. An isolated human anti-human influenza virus monoclonal antibody according to claim 1, wherein the isolated antibody comprises an isolated intact antibody.

6. A composition comprising the isolated human anti-human influenza virus monoclonal antibody according to claim 1 and a pharmaceutically acceptable carrier.

7. A hybridoma that produces the isolated human anti-human influenza virus monoclonal antibody according to claim 1.

8. The isolated human anti-human influenza virus monoclonal antibody according to claim 1, wherein the isolated antibody is a humanized or chimeric antibody.

9. A composition comprising the isolated human anti-human influenza virus monoclonal antibody according to claim 1, and at least one preservative.

10. A composition comprising the isolated human anti-human influenza virus monoclonal antibody according to claim 1, and at least one stabilizer.

11. An isolated DNA encoding a variable region of an isolated human anti-human influenza virus monoclonal antibody comprising a neutralization activity against a human influenza B virus, the DNA comprising a base sequence set forth in any one of SEQ ID NOS: 9 to 12 or a sequence having substitutions of one or more nucleotides in the base sequence, and which encodes SEQ ID NOS: 31-34, respectively.

12. The isolated DNA according to claim 11, wherein the isolated DNA is a cDNA.

* * * * *